US011141107B2

(12) United States Patent
Arnold et al.

(10) Patent No.: US 11,141,107 B2
(45) Date of Patent: Oct. 12, 2021

(54) PRESENTING HEALTH RELATED MESSAGES TO USERS OF AN ACTIVITY/HEALTH MONITORING PLATFORM

(71) Applicant: Fitbit, Inc., San Francisco, CA (US)

(72) Inventors: Jacob Arnold, Sunnyvale, CA (US); Yasaman Baiani, Lafeyette, CA (US); Yeqing Cheng, San Carlos, CA (US)

(73) Assignee: Fitbit, Inc., San Francisco, CA (US)

( * ) Notice: Subject to any disclaimer, the term of this patent is extended or adjusted under 35 U.S.C. 154(b) by 101 days.

(21) Appl. No.: 15/684,705

(22) Filed: Aug. 23, 2017

(65) Prior Publication Data

US 2018/0256095 A1 Sep. 13, 2018

Related U.S. Application Data

(60) Provisional application No. 62/468,349, filed on Mar. 7, 2017.

(51) Int. Cl.
*A61B 5/00* (2006.01)
*A63B 24/00* (2006.01)
(Continued)

(52) U.S. Cl.
CPC .......... *A61B 5/486* (2013.01); *A61B 5/02055* (2013.01); *A61B 5/02438* (2013.01); *A61B 5/112* (2013.01); *A61B 5/4806* (2013.01); *A61B 5/4809* (2013.01); *A61B 5/4812* (2013.01); *A61B 5/4815* (2013.01); *A61B 5/4818* (2013.01); *A63B 24/0062* (2013.01); *A63B 71/0622* (2013.01); *G16H 40/63* (2018.01); *G16H 50/30* (2018.01); *A61B 5/021* (2013.01); *A61B 5/02405* (2013.01); *A61B 5/0816* (2013.01); *A61B 5/14532* (2013.01); (Continued)

(58) Field of Classification Search
None
See application file for complete search history.

(56) References Cited

U.S. PATENT DOCUMENTS

| 6,491,647 | B1 * | 12/2002 | Bridger | A61B 5/021 |
| | | | | 128/900 |
| 9,782,122 | B1 * | 10/2017 | Pulliam | A61B 5/1112 |
| 2008/0306351 | A1 * | 12/2008 | Izumi | A61B 5/6892 |
| | | | | 600/300 |

* cited by examiner

*Primary Examiner* — James B Hull
(74) *Attorney, Agent, or Firm* — Dority & Manning, P.A.

(57) ABSTRACT

Selecting and presenting messages to user of an activity/health monitoring platform. The health/activity monitoring platform may receive physiological data for a user. The health/activity monitoring platform may identify a set of messages based on the physiological data. The health/activity monitoring platform may also determine a set of scores for the set of messages. Each score from the set of scores may be associated with a message from the set of messages and each score from the set of scores may be indicative of whether a respective message should be presented to the user. The health/activity monitoring platform may also identify a first message from a set of messages based on the set of scores and cause the first message to be presented via a display of a computing device of the user. The health/activity monitoring platform may also update a first set of penalties associated with the first message in response to causing the first message to be presented. The first set of penalties decreases a first likelihood that the first message will be presented to the user again.

27 Claims, 14 Drawing Sheets

(51) Int. Cl.
*A63B 71/06* (2006.01)
*A61B 5/0205* (2006.01)
*A61B 5/11* (2006.01)
*A61B 5/024* (2006.01)
*G16H 40/63* (2018.01)
*G16H 50/30* (2018.01)
*A61B 5/021* (2006.01)
*A61B 5/08* (2006.01)
*A61B 5/145* (2006.01)

(52) U.S. Cl.
CPC ......... *A61B 5/14546* (2013.01); *A61B 5/6824* (2013.01); *A61B 5/743* (2013.01); *A61B 5/7435* (2013.01); *A63B 2024/0065* (2013.01); *A63B 2071/0625* (2013.01); *A63B 2220/17* (2013.01); *A63B 2220/62* (2013.01); *A63B 2220/72* (2013.01); *A63B 2220/75* (2013.01); *A63B 2220/76* (2013.01)

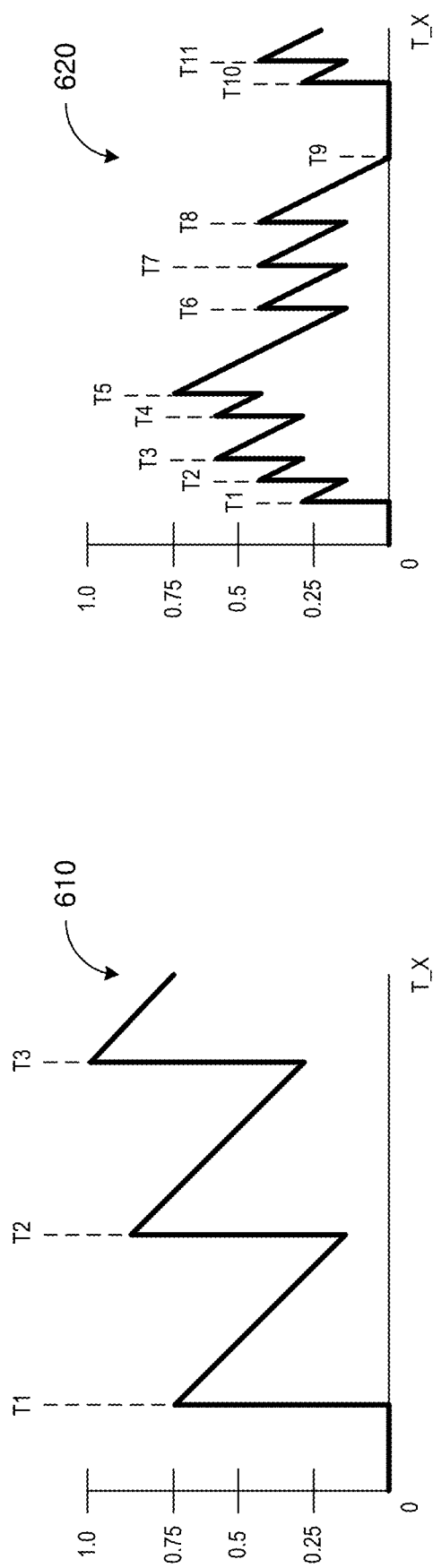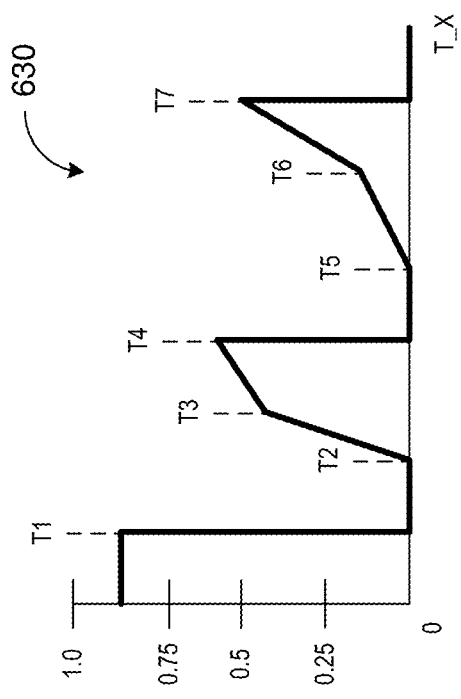
FIG. 6A
FIG. 6B
FIG. 6C

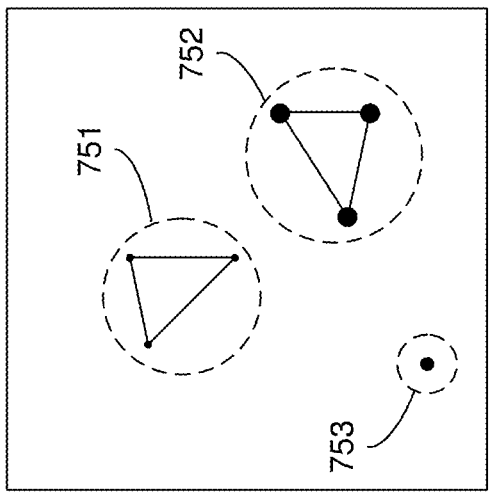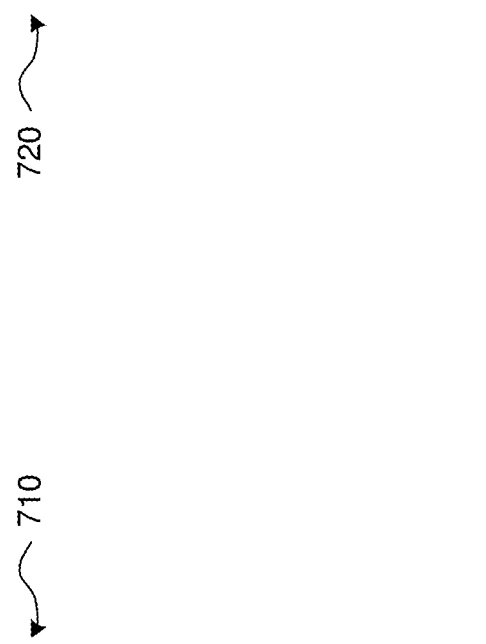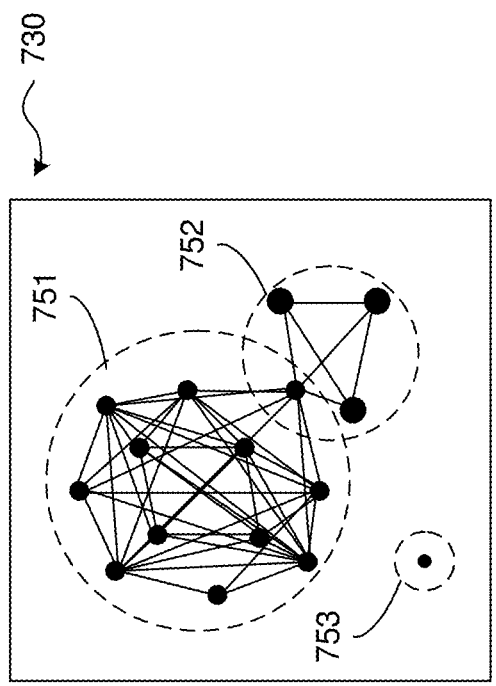

PRESENTING HEALTH RELATED MESSAGES TO USERS OF AN ACTIVITY/HEALTH MONITORING PLATFORM

CROSS-REFERENCE TO RELATED APPLICATIONS

This application claims priority to U.S. Provisional Patent Application No. 62/468,349 filed Mar. 7, 2017, entitled SELECTING CONTENT FOR PRESENTATION TO A USER. The contents of the above-referenced application is hereby expressly incorporated by reference in its entirety for all purposes.

BACKGROUND

Field

The present disclosure generally relates to the field of computing devices with one or more sensors to collect physiological information of a user.

Description of Related Art

Computing devices, such as wearable computing devices, can incorporate or interact with one or more sensors for receiving physiological information of a user, used for making health-based assessments.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 6A is a graph that illustrates changes to a recency penalty over time, in accordance with one or more embodiments.

FIG. 6B is a graph that illustrates changes to a subject matter penalty over time, in accordance with one or more embodiments.

FIG. 6C is a graph that illustrates changes to a score over time, in accordance with one or more embodiments.

FIG. 7A is a graph that illustrates messages which may be identified for a user of the health/activity monitoring platform, in accordance with one or more embodiments.

FIG. 7B is a graph that illustrates messages which may be identified for a user of the health/activity monitoring platform, in accordance with one or more embodiments.

FIG. 7C is a graph that illustrates messages which may be identified for a user of the health/activity monitoring platform, in accordance with one or more embodiments.

DETAILED DESCRIPTION

Figure 1:
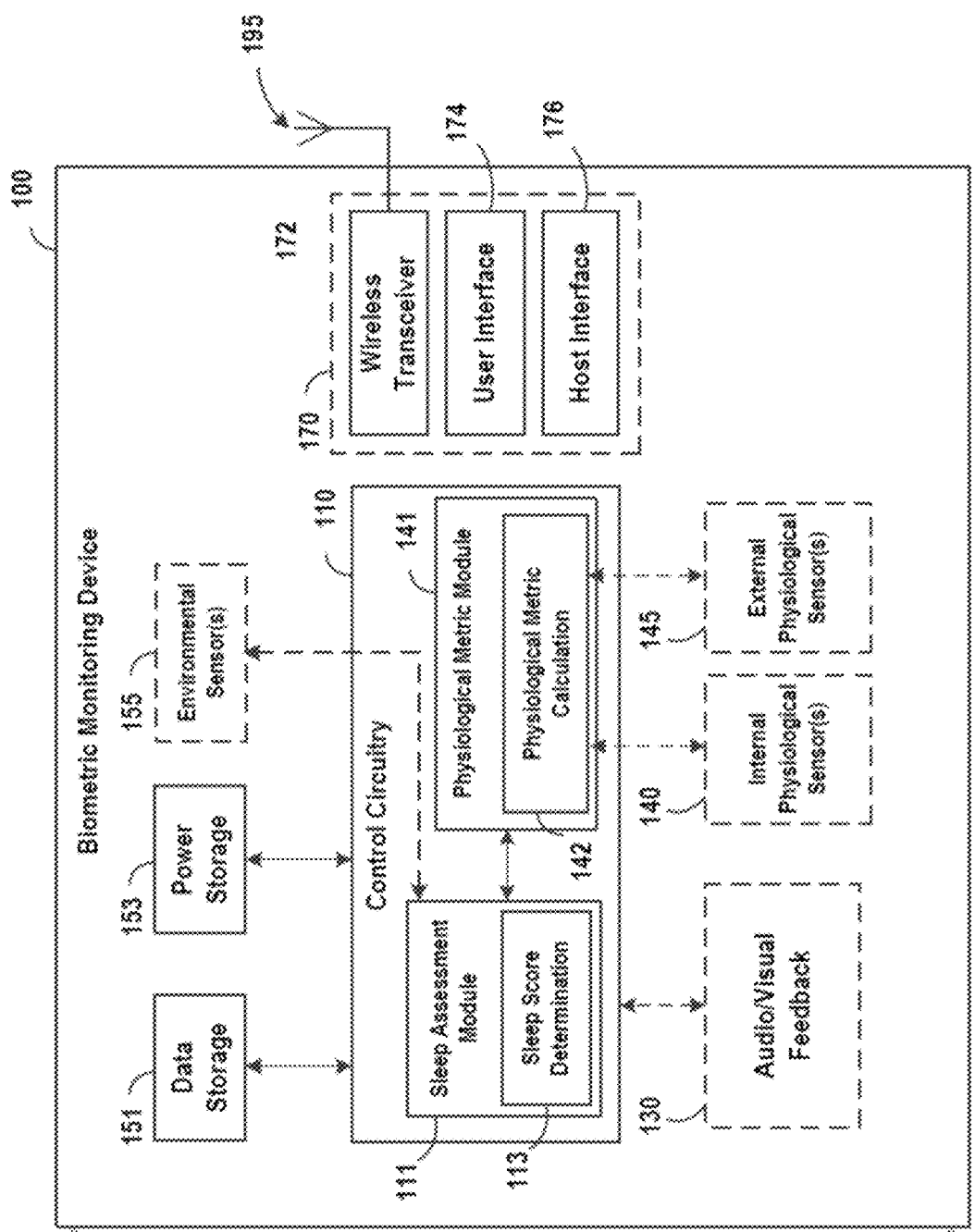
FIG. 1 is a block diagram illustrating an embodiment of a computing device, in accordance with one or more embodiments.

The headings provided herein are for convenience only and do not necessarily affect the scope or meaning of the claimed invention. Like reference numbers and designations in the various drawings may or may not indicate like elements.

Although certain embodiments, implementations, and/or examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

As computing devices become more ubiquitous and portable, many advantages are being seen in the field of health monitoring and diagnostics. Computing devices, particularly ones that can be worn or carried by a user, may include one or more sensors to detect physiological information about the user and/or the environment around the user. This information can be used to observe, detect or diagnose various health conditions outside of a traditional clinic or laboratory setting. For example, in the context of sleep therapy, a portable or wearable electronic device may be able to detect when a user moves at night, or monitor various physiological factors such as a heart rate. Additionally, a computing device may be able to record and interpret the detected information about the user and/or environment, to determine a health assessment. As in the previous example, a wearable electronic device may be able to record a relatively high frequency of movement while the user is sleeping, and generate an assessment that the user did not have a restful period of sleep.

The users and the computing devices may be part of a health/activity monitoring platform. The health/activating monitoring platform may monitor/track the health, activity (e.g., physical activity), diet, etc., of the users. For example, the computing devices may collect data (e.g., physiological data, behavioral data, environmental data, etc.) for the users and may provide the data to one or more server systems/computers of the health/activity monitoring platform. The server systems/computers may determine how much users exercise, sleep, eat, etc., based on the data.

In one embodiment, the health/activity monitoring platform may present the users (of the health/activity monitoring platform) with messages (e.g., health related content or information) to help improve and/or maintain the health of the users. For example, the health/activity monitoring platform may present the users with recommended health goals (e.g., sleep at least 7 hours a day, walk/run at least one mile a day, etc.). In another example, the health/activity monitoring platform may provide the user with motivational messages to help encourage the user. In a further example, the health/activity monitoring platform may present the user with status/informational messages to inform the user of their current progress in meeting a health/fitness goal. As more and more messages are present to the user (by the health/activity monitoring platform), the same message may be repeatedly presented to the user. For example, every time the user achieves a goal, the same congratulatory message may be presented to the user. In addition, some systems may select messages that may not be relevant to the user. For example, the system present generic messages that may not be useful or relevant to the user. If a user continually sees the same message or is continually presented with messages that may not be interesting/applicable to the user, the user may begin to ignore/disregard the messages that are presented by the health/activity monitoring platform. Thus, it may be useful for the health/activity monitoring platform to reduce the number of times that the same message may be presented to the user and/or to identify content that may be useful/relevant to the user. It may also be useful for the health/activity monitoring platform to identify new messages (that the user has not seen before) to present to the user. This may help keep the user interested in reading the messages (which may provide the user with useful information, may help motivate a user, may help the user achieve health/fitness goals, etc.).

Portable Computing Devices

FIG. 1 is a block diagram illustrating an embodiment of a computing device 100, in accordance with one or more embodiments disclosed herein. In certain embodiments, the computing device 100 may be worn by a user 10, such as with respect to embodiments in which the computing device 100 is a wearable biometric or physiological monitoring device. For example, the computing device 100 may comprise a wearable biometric monitoring device configured to gather data regarding activities performed by the wearer, or regarding the wearer's physiological state. The computing device 100 may be a biometric monitoring device. Such data may include data representative of the ambient environment around the wearer or the wearer's interaction with the environment. For example, the data may comprise motion data regarding the wearer's movements, ambient light, ambient noise, air quality, etc., and/or physiological data obtained by measuring various physiological characteristics of the wearer, such as heart rate, body temperature, blood oxygen levels, perspiration levels, and the like. Although certain embodiments are disclosed herein in the context of wearable biometric monitoring devices, it should be understood that biometric/physiological monitoring and health assessment principles and features disclosed herein may be applicable with respect to any suitable or desirable type of computing device or combination of computing devices, whether wearable or not.

The computing device 100 may include one or more audio/visual feedback modules 130, such as electronic touchscreen display units, light-emitting diode (LED) display units, audio speakers, LED lights or buzzers. In certain embodiments, the one or more audio/visual feedback modules 130 may be associated with the front side of the computing device 100. For example, in wearable embodiments of the computing device 100, an electronic display may be configured to be externally presented to a user viewing the computing device 100.

The computing device 100 includes control circuitry 110. Although certain modules and/or components are illustrated as part of the control circuitry 110 in the diagram of FIG. 1, it should be understood that control circuitry associated with the computing device 100 and/or other components or devices in accordance with the present disclosure may include additional components and/or circuitry, such as one or more of the additional illustrated components of FIG. 1. Furthermore, in certain embodiments, one or more of the illustrated components of the control circuitry 110 may be omitted and/or different than that shown in FIG. 1 and described in association therewith. The term "control circuitry" is used herein according to its broad and/or ordinary meaning, and may include any combination of software and/or hardware elements, devices or features, which may be implemented in connection with operation of the computing device 100. Furthermore, the term "control circuitry" may be used substantially interchangeably in certain contexts herein with one or more of the terms "controller," "integrated circuit," "IC," "application-specific integrated circuit," "ASIC," "controller chip," or the like.

The control circuitry 110 may comprise one or more processors, data storage devices, and/or electrical connections. For example, the control circuitry 110 may comprise one or more processors configured to execute operational code for the computing device 100, such as firmware or the like, wherein such code may be stored in one or more data storage devices of the computing device 100. In one embodiment, the control circuitry 110 is implemented on an SoC (system on a chip), though those skilled in the art will recognize that other hardware/firmware implementations are possible.

The control circuitry 110 may comprise a sleep score determination module 113. The sleep score determination module 113 may comprise one or more hardware and/or software components or features configured to make an assessment of sleep quality of a user, optionally using inputs from one or more environmental sensors 155 (e.g., ambient light sensor) and information from the physiological metric module 141. In certain embodiments, the sleep assessment module 111 includes a sleep score determination module 113 configured to determine a unified sleep quality score, using information accumulated by the sleep assessment module 111, such as the values of one or more physiological metrics determined by the physiological metric calculation module 142 of the physiological metric module 141. In certain embodiments, the physiological metric module 141 is optionally in communication with one or more internal physiological sensors 140 embedded or integrated in the computing device 100. In certain embodiments, the physiological metric module 141 is optionally in communication with one or more external physiological sensors 145 not embedded or integrated in the computing device 100 (e.g., an electrode, or sensor integrated in another electronic device). Examples of internal physiological sensors 140 and external physiological sensors 145 include, but are not limited to, sensors for measuring body temperature, heart rate, blood oxygen level and movement.

The computing device may further comprise data storage 151, which may include any suitable or desirable type of data storage, such as solid-state memory, which may be volatile or non-volatile. Solid-state memory of the computing device 100 may comprise any of a wide variety of technologies, such as flash integrated circuits, Phase Change Memory (PC-RAM or PRAM), Programmable Metallization Cell RAM (PMC-RAM or PMCm), Ovonic Unified Memory (OUM), Resistance RAM (RRAM), NAND memory, NOR memory, EEPROM, Ferroelectric Memory (FeRAM), MRAM, or other discrete NVM (non-volatile solid-state memory) chips. The data storage 151 may be used to store system data, such as operating system data and/or system configurations or parameters. The computing device 100 may further comprise data storage utilized as a buffer and/or cash memory for operational use by the control circuitry 110.

The computing device 100 further comprises power storage 153, which may comprise a rechargeable battery, one or more capacitors, or other charge-holding device(s). The power stored by the power storage 153 maybe utilized by the control circuitry 110 for operation of the computing device 100, such as for powering the touchscreen display 130. The power storage 153 may receive power over the host interface 176 or through other means.

The computing device 100 may comprise one or more environmental sensors 155. Examples of such environmental sensors 155 include, but are not limited to sensors for measuring ambient light, external (non-body) temperature, altitude and global-positioning system (GPS) data.

The computing device 100 may further comprise one or more connectivity ciricuitry 170, which may include, for example, a wireless transceiver 172. The wireless transceiver 172 may be communicatively coupled to one or more antenna devices 195, which may be configured to wirelessly transmit/receive data and/or power signals to/from the computing device using, but not limited to peer-to-peer, WLAN or cellular communications. For example, the wireless transceiver 172 maybe utilized to communicate data and/or power between the computing device 100 and an external host system (not shown), which may be configured to interface with the computing device 100. In certain embodiments, the computing device 100 may comprise additional host interface circuitry and/or components, such as wired interface components for communicatively coupling with a host device or system to receive data and/or power therefrom and/or transmit data thereto.

The connectivity circuitry 170 may further comprise user interface 174 for receiving user input. For example, the user interface 174 may be associated with one or more audio/visual feedback modules 130, wherein the touchscreen display is configured to receive user input from user contact therewith. The user interface 174 may further comprise one or more buttons or other input components or features.

The connectivity circuitry 170 may further comprise the host interface 176, which may be, for example, an interface for communicating with a host device or system (not shown) over a wired or wireless connection. The host interface 176 may be associated with any suitable or desirable communication protocol and/or physical connector, such as Universal Serial Bus (USB), Micro-USB, WiFi, Bluetooth, FireWire, PCIe, or the like. For wireless connections, the host interface 176 may be incorporated with the wireless transceiver 172.

Although certain functional modules and components are illustrated and described herein, it should be understood that authentication management functionality in accordance with the present disclosure may be implemented using a number of different approaches. For example, in some implementations the control circuitry 110 may comprise one or more processors controlled by computer-executable instructions stored in memory so as to provide functionality such as is described herein. In other implementations, such functionality may be provided in the form of one or more specially-designed electrical circuits. In some implementations, such functionality may be provided by one or more processors controlled by computer-executable instructions stored in a memory coupled with one or more specially-designed electrical circuits. Various examples of hardware that may be used to implement the concepts outlined herein include, but are not limited to, application specific integrated circuits (ASICs), field-programmable gate arrays (FPGAs), and general-purpose microprocessors coupled with memory that stores executable instructions for controlling the general-purpose microprocessors.

Wearable Computing Devices

In some implementations, a portable computing device, such as computing device 100 of FIG. 1, may be designed so that it can be inserted into a wearable case or into one or more of multiple different wearable cases (e.g., a wristband case, a belt-clip case, a pendant case, a case configured to be attached to a piece of exercise equipment such as a bicycle, etc.). In other implementations, a portable computing device may be designed to be worn in limited manners, such as a computing device that is integrated into a wristband in a non-removable manner, and may be intended to be worn specifically on a person's wrist (or perhaps ankle). Irrespective of configuration, wearable computing devices having one or more physiological and/or environmental sensors may be configured to collect physiological and/or environmental data in accordance with various embodiments disclosed herein. Wearable computing devices may also be configured to analyze and interpret collected physiological and/or environmental data to perform a sleep quality assessment of a user (e.g., wearer) of the computing device, or may be configured to communicate with another computing device or server that performs the sleep quality assessment.

Figure 2A:
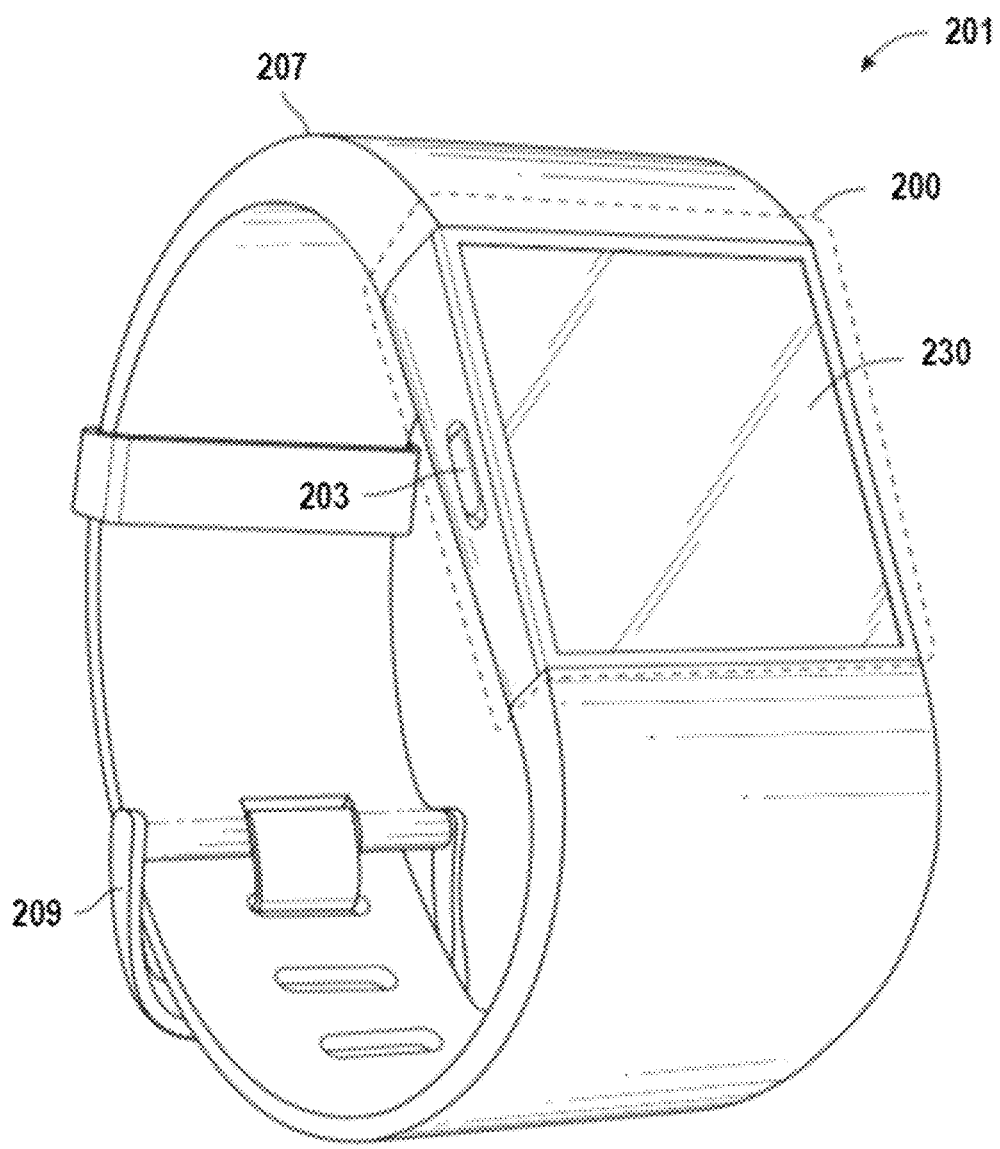
FIG. 2A shows perspective front and side views of a wearable computing device, in accordance with one or more embodiments.

Wearable computing devices according to embodiments and implementations described herein may have shapes and sizes adapted for coupling to (e.g., secured to, worn, borne by, etc.) the body or clothing of a user. An example of a wearable computing device 201 is shown in FIG. 2A. FIG. 2A shows perspective front and side views of the wearable computing device 201. The wearable computing device 201 includes both a computing device 200, as well as a band portion 207. In certain embodiments, the band portion 207 includes first and second portions that may be connected by a clasp portion 209. The computing device portion 200 may be insertable, and may have any suitable or desirable dimensions. Wearable computing devices may generally be relatively small in size so as to be unobtrusive for the wearer, and therefore, an optional touchscreen display 230 may be relatively small in size relative to certain other computing devices. The biometric monitoring device 200 (e.g., a computing device or a wearable computing device) may be designed to be able to be worn without discomfort for long periods of time and to not interfere with normal daily activity or with sleep.

The electronic display 230 may comprise any type of electronic display known in the art. For example, the display 230 may be a liquid crystal display (LCD) or organic light emitting diode (OLED) display, such as a transmissive LCD or OLED display. The electronic display 230 may be configured to provide brightness, contrast, and/or color saturation features according to display settings maintained by control circuitry and/or other internal components/circuitry of the computing device 200.

The touchscreen 230 may be a capacitive touchscreen, such as a surface capacitive touchscreen or a projective capacitive touch screen, which may be configured to respond to contact with electrical charge-holding members or tools, such as a human finger.

Wearable computing devices, such as biometric monitoring devices, in accordance with the present disclosure may incorporate one or more existing functional components or modules designed for determining one or more physiological metrics associated with a user (e.g., wearer) of the device, such as a heart rate sensor (e.g., photoplethysmograph sensor), body temperature sensor, environment temperature sensor or the like. Such components/modules may be disposed or associated with an underside/backside of the biometric monitoring device, and may be in contact or substantially in contact with human skin when the biometric monitoring device is worn by a user. For example, where the biometric monitoring device is worn on the user's wrist, the physiological metric component(s)/module(s) may be associated with an underside/backside of the device substantially opposite the display and touching the arm of the user.

In one embodiment, the physiological and/or environmental sensors (sources and/or detectors) may be disposed on an interior or skin-side of the wearable computing device (i.e., a side of the computing device that contacts, touches, and/or faces the skin of the user (hereinafter "skin-side"). In another embodiment, the physiological and/or environmental sensors may be disposed on one or more sides of the device, including the skin-side and one or more sides of the device that face or are exposed to the ambient environment (environmental side).

Figure 2B:
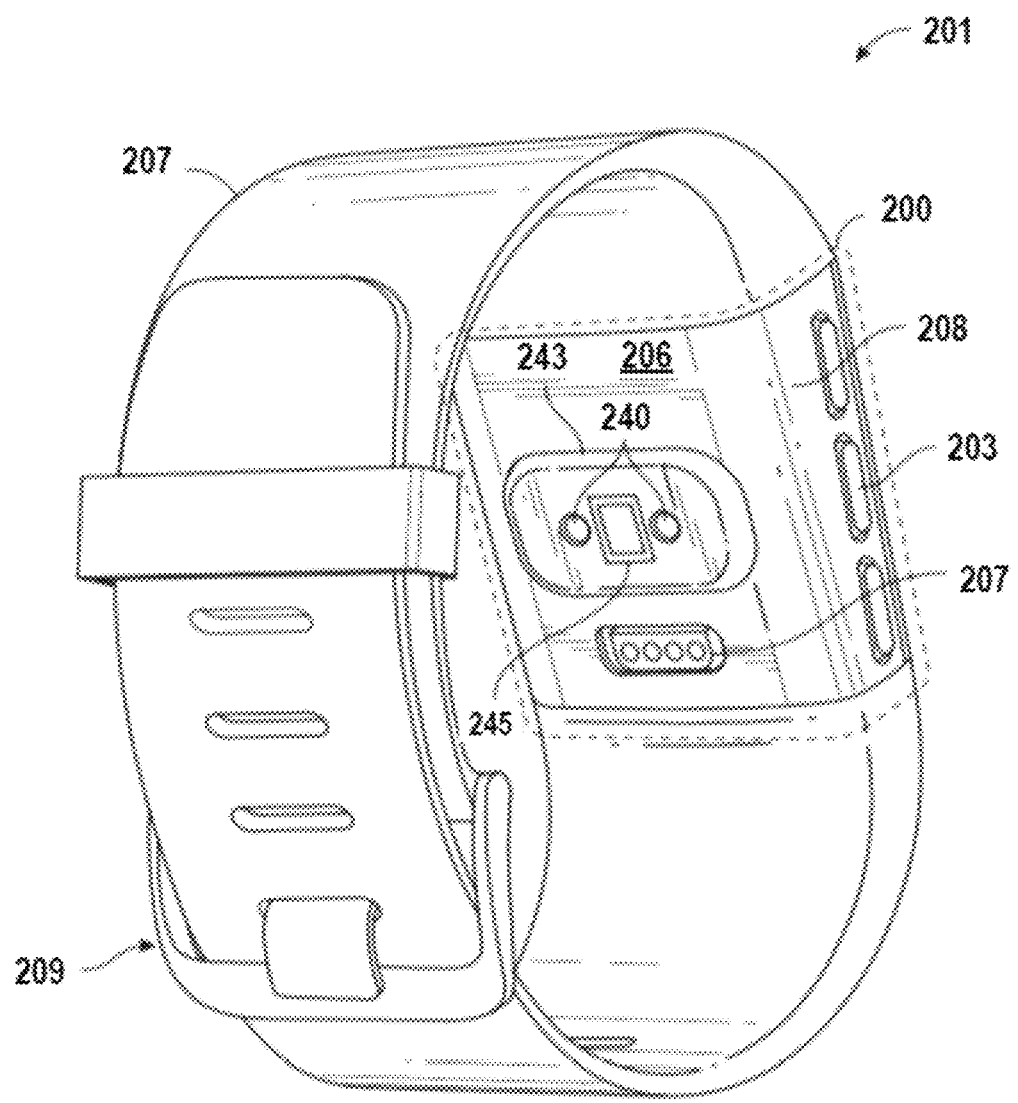
FIG. 2B shows perspective back and side views of a wearable computing device, in accordance with one or more embodiments.

FIG. 2B is a perspective back and side view of the wearable biometric monitoring device 201 of FIG. 2A. The wearable biometric monitoring device 201 comprises a band portion 207, which may be configured to be latched or secured about a user's arm or other appendage via a securement mechanism of any suitable or desirable type. For example, the band 207 may be secured using a hook and loop clasp component 209. In certain embodiments, the band 207 is designed with shape memory to promote wrapping around the user's arm.

The wearable biometric monitoring device 201 includes a biometric monitoring device component 200, which may be at least partially secured to the band 207. The view of FIG. 2B shows a backside 206 (also referred to herein as the "underside") of the biometric monitoring device 200, which may generally face and/or contact skin or clothing associated with the user's arm, for example. The terms "backside" and "underside" are used herein according to their broad and ordinary meaning, and may be used in certain contexts to refer to a side, panel, region, component, portion and/or surface of a biometric monitoring device that is positioned and/or disposed substantially opposite to a user display screen, whether exposed externally of the device, or at least partially internal to an electronics package or housing of the device.

The wearable biometric monitoring device 201 may include one or more buttons 203, which may provide a mechanism for user input. The wearable biometric monitoring device 201 may further comprise a device housing, which may comprise one or more of steel, aluminum, plastic, and/or other rigid structure. The housing 208 may serve to protect the biometric monitoring device 200 and/or internal electronics/components associated therewith from physical damage and/or debris. In certain embodiments, the housing 208 is at least partially waterproof.

The backside 206 of the biometric monitoring device 200 may have an optical physiological metric sensor 243 associated therewith, which may comprise one or more sensor components, such as one or more light sources 240 and/or light detectors 245, the collection of which may represent an example of an internal physiological sensor 140 of FIG. 1. In certain embodiments, the optical physiological metric sensor 243 comprises a protrusion form protruding from the back surface of the biometric monitoring device 200. The sensor components may be used to determine one or more physiological metrics of a user wearing the wearable biometric monitoring device 201. For example, the optical physiological sensor components associated with the sensor 243 may be configured to provide readings used to determine heart rate (e.g., in beats-per-minute (BPM)), blood oxygenation (e.g., $SpO_2$), blood pressure, or other metric. In certain embodiments, the biometric monitoring device 200 further includes an electrical charger mating recess 207.

Although the sensor 243 is illustrated as comprising a protrusion from certain figures herein, it should be understood that backside sensor modules in accordance with the present disclosure may or may not be associated with a protrusion form. In certain embodiments, the protrusion form on the backside of the device may be designed to engage the skin of the user with more force than the surrounding device body. In certain embodiments, an optical window or light-transmissive structure may be incorporated in a portion of the protrusion 243. The light emitter(s) 240 and/or detector(s) 245 of the sensor module 243 may be disposed or arranged in the protrusion 243 near the window or light-transmissive structure. As such, when attached to the user's body, the window portion of the protrusion 243 of the biometric monitoring device 200 may engage the user's skin with more force than the surrounding device body, thereby providing a more secure physical coupling between the user's skin and the optical window. That is, the protrusion 243 may cause sustained contact between the biometric monitoring device and the user's skin that may reduce the amount of stray light measured by the photodetector 245, decrease relative motion between the biometric monitoring device 200 and the user, and/or provide improved local pressure to the user's skin, some or all of which may increase the quality of the cardiac signal of interest generated by the sensor module. Notably, the protrusion 243 may contain other sensors that benefit from close proximity and/or secure contact to the user's skin. These may be included in addition to or in lieu of a heart rate sensor and may include sensors such as a skin temperature sensor (e.g., noncontact thermopile that utilizes the optical window or thermistor joined with thermal epoxy to the outer surface of the protrusion), pulse oximeter, blood pressure sensor, EMG, or galvanic skin response (GSR) sensor.

Collecting Physiological and/or Environmental Information

The wearable computing device 201 may be configured to collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing the wearable computing device 201, the wearable computing device 201 may calculate and store the user's step count using one or more biometric sensors. The wearable computing device 201 may then transmit data representative of the user's step count to an account on a web service, computer, mobile phone, or health station where the data may be stored, processed, and visualized by the user. Indeed, the wearable computing device 201 may measure or calculate a plurality of other physiological metrics in addition to, or in place of, the user's step count. These include, but are not limited to, energy expenditure, e.g., calorie burn, floors climbed and/or descended, heart rate, heart rate variability, heart rate recovery, location and/or heading, e.g., through GPS or a similar system, elevation, ambulatory speed and/or distance traveled, swimming lap count, swimming stroke type and count detected, bicycle distance and/or speed, blood pressure, blood glucose, skin conduction, skin and/or body temperature, muscle state measured via electromyography, brain activity as measured by electroencephalography, weight, body fat, caloric intake, nutritional intake from food, medication intake, sleep periods, e.g., clock time, sleep phases, sleep quality and/or duration, pH levels, hydration levels, respiration rate, and other physiological metrics.

The wearable computing device 201 may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field. Furthermore, the wearable computing device 201 or the system collating the data streams from the wearable computing device 201 may calculate metrics derived from such data. For example, the device or system may calculate the user's stress and/or relaxation levels through a combination of heart rate variability, skin conduction, noise pollution, and body temperature. Similarly, the wearable computing device 201 or the system collating the data streams from the wearable computing device 201 may determine values corresponding to sleep quality metrics derived from such data. For example, the device or system may calculate the user's restlessness and/or quality of rapid-eye movement (REM) sleep through a combination of heart rate variability, blood oxygen level, sleep duration, and body temperature. In another example, the wearable computing device 201 may determine the efficacy of a medical intervention, e.g., medication, through the combination of medication intake, sleep data, and/or activity data. In yet another example, the biometric monitoring device or system may determine the efficacy of an allergy medication through the combination of pollen data, medication intake, sleep and/or activity data. These examples are provided for illustration only and are not intended to be limiting or exhaustive. Further embodiments and implementations of sensor devices may be found in U.S. Pat. No. 9,167,991, titled "Portable Biometric Monitoring Devices and Methods of Operating Same" filed Jun. 8, 2011, which is hereby incorporated herein by reference in its entirety.

Presenting Messages to a User of a Health/Activity Monitoring Platform

Figure 3:
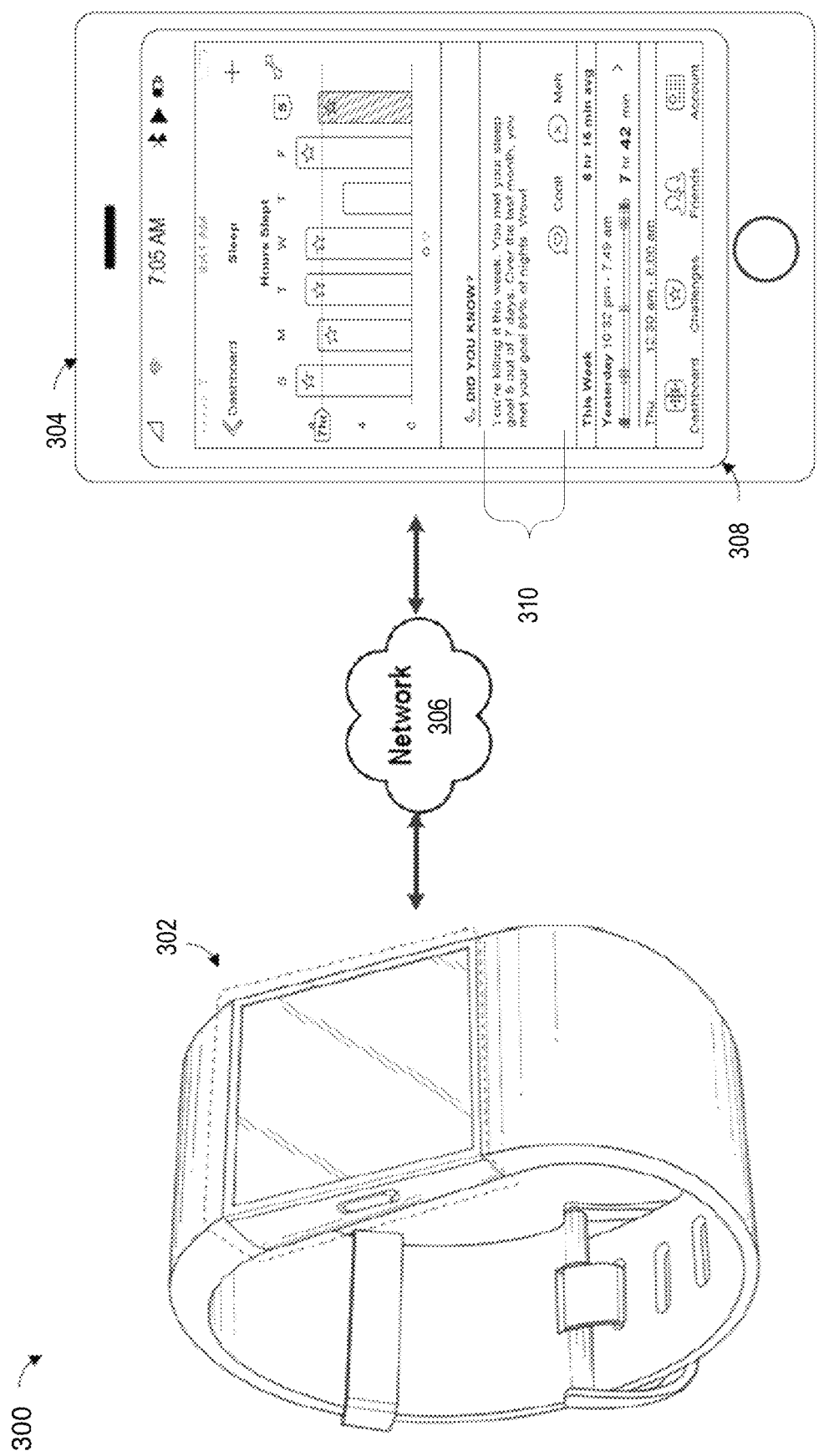
FIG. 3 illustrates a networked relationship between a wearable computing device and an external computing device, in accordance with one or more embodiments.

FIG. 3 illustrates a networked relationship 300 between a wearable computing device 302 and an external computing device 304, in accordance with one or more embodiments. The wearable computing device 302 may be configured to collect one or more types of physiological and/or environmental data from embedded sensors and/or external devices, as described throughout the present disclosure, and communicate or relay such information over network 306 to other devices. This includes, in some implementations, relaying information to devices capable of serving as Internet-accessible data sources, thus permitting the collected data to be viewed, for example, using a web browser or network-based application at an external computing device 304. For example, while the user is asleep and wearing the wearable computing device 302, the wearable computing device 302 may calculate and optionally store the user's sleeping heart rate using one or more biometric sensors. The wearable computing device 302 may then transmit data representative of the user's sleeping heart rate over network 306 to an account on a web service, computer, mobile phone, or health station where the data may be stored, processed, and visualized by the user.

While the example wearable computing device 302 is shown to have a touchscreen display, it should be understood that the wearable computing device 302 may not have any type of display unit, or may have any variety of audio and/or visual feedback components, such as light-emitting diodes (LEDs) (of various colors), buzzers, speakers, or a display with limited functionality. The wearable computing device 302 may be configured to be attached to the user's body, or clothing, such as a wrist bracelet, watch, ring, electrode, finger-clip, toe-clip, chest-strap, ankle strap or a device placed in a pocket. Additionally, the wearable computing device 302 may alternatively be embedded in something in contact with the user such as clothing, a mat under the user, a blanket, a pillow or another accessory involved in the activity of engaging in sleep. In other embodiments, other devices may be used to collect physiological data, environmental data, and/or behavioral data. For example, a bedside monitor (e.g., a monitoring device) may include one or more of a camera, motion sensors, temperature sensors (e.g., thermometers), humidity sensors, a microphone, etc.

The communication between wearable computing device 302 and external device 304 may be facilitated by the network 306. In some implementations, the network 306 may include one or more of an ad hoc network, a peer to peer communication link, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or any other type of network. The communication between the wearable computing device 302 and external device 304 may also be performed through a direct wired connection. This direct-wired connection may be associated with any suitable or desirable communication protocol and/or physical connector, such as Universal Serial Bus (USB), Micro-USB, WiFi, Bluetooth, FireWire, PCIe, or the like.

A variety of computing devices may be in communication with the wearable computing device 302, to facilitate sleep quality assessment. As depicted in FIG. 3, an example external computing device 304 is a smart phone with a display 308. An external computing device 304 may be any computing device capable of presenting messages (e.g., insights, content, etc.) to a user. Examples of external computing devices include, but are not limited to, a smart phone, personal digital assistant (PDA), a mobile phone, a tablet, a personal computer, a laptop computer, a smart television, and/or a video game console. This example external computing device 304 illustrates that in some embodiments, through this networked relationship shown in FIG. 3, an external computing device 304 may be implemented to present messages (e.g., health related messages and/or content) to a user. For example, a user wears a wearable computing device 302 equipped as a bracelet with one or more physiological sensors but without a display. In this example, over the course of the night, as the user sleeps, the wearable computing device 302 records the user's heartbeat, movement, body temperature and blood oxygen level as well as room temperature and ambient light levels, and periodically transmits this information to the external computing device 304. Alternatively, the wearable computing device 302 may store and transmit the collected physiological and/or environmental data and transmit this data to the external computing device 304 in response to a trigger, such as detection of the user being awake after a period of being asleep. In some implementations, the user must be awake for a threshold period of time to set this trigger (e.g., awake for at least 10 minutes), and/or awake for a threshold period of time after a threshold period of sleep has been experienced (e.g., awake for at least 5 minutes after having at least 6 hours of sleep).

The example external computing device 304 illustrates that in some implementations, the external computing device 304 may present a message 310 via the display 308. This presentation may be made to the user (e.g., wearer) of the wearable computing device 302 and/or the computing device 304. The message 310 may include content (e.g., text, images, movies, multimedia, etc.) provided by a health/activity monitoring platform (not illustrated in FIG. 3). For example, the health/activity monitoring platform may generate the message 310 and transmit the message 310 to the external computing device 304 via the network 306 or may transmit data/information to instruct/cause the computing device 304 to present/display the message 310. The message 310 may provide various types of information to the user of the wearable computing device 302. For example, the message 310 may include motivational/informational messages to encourage a user (e.g., encourage a user to reach a health/fitness goal). In another example, the health/activity monitoring platform may present the user with status messages to inform the user of their current progress in meeting a health/fitness goal. In a further example, the health/activity monitoring platform may present the user with informational messages that may provide information and/or tips about health related topics (e.g., tips for getting a better night's sleep, etc.). In another example, the health/activity monitoring platform may present the users with recommended health goals (e.g., sleep at least 7 hours a day, walk/run at least one mile a day, etc.).

In one embodiment, the messages presented by the health/activity monitoring platform may generally be health related. The message 310 may also be referred to as an insight or an insight message. Although the message 310 is presented by the computing device 304, the message 310 may also be presented by the wearable computing device 302 in other embodiments.

As discussed above, the user may begin to ignore/disregard the messages that are presented by the health/activity monitoring platform if the user continually sees the same message or is continually presented with messages that may not be interesting/applicable to the user. Thus, it may be useful for the health/activity monitoring platform to reduce the number of times that the same message may be presented to the user and/or to identify new content that may be useful/relevant to the user.

Although the messages, topics/subject matters, physiological data, behavioral data, environmental data, user data, and feedback data described herein may refer to a user's sleep, one having ordinary skill in the art understands that the examples, implementations, and/or embodiments described herein may be applied to other types of health related concepts. For example, the messages and topics/subject matters may be related to physical activities/exercises. In another example, the messages and topics/subject matters may be related to a user's diet or eating habits.

Figure 4:
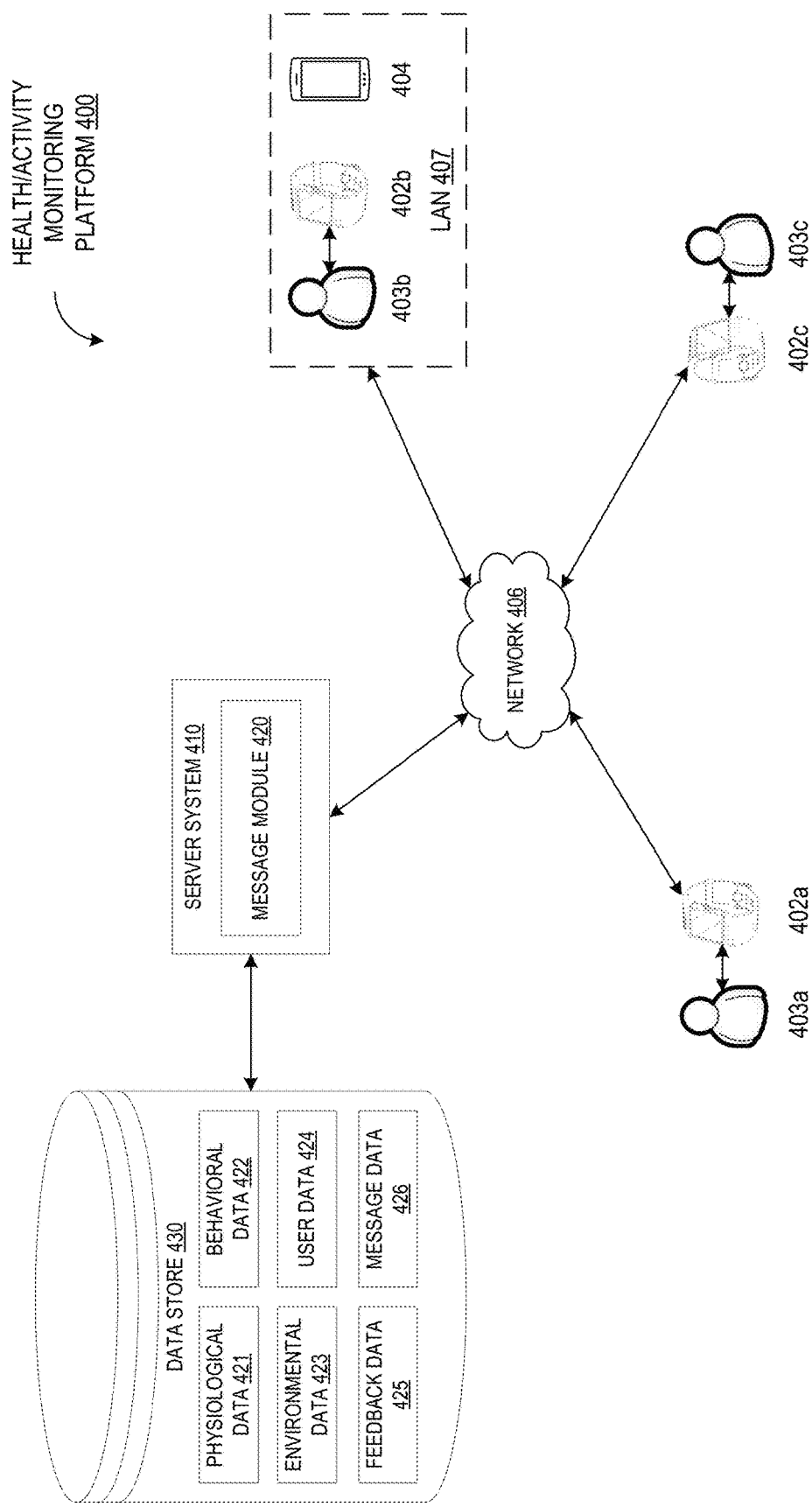
FIG. 4 illustrates a health/activity monitoring platform, in accordance with one or more embodiments.

FIG. 4 illustrates a health/activity monitoring platform 400, in accordance with one or more embodiments. In certain implementations, the health/activity monitoring platform 400 may be implemented across a plurality of electronic devices. The health/activity monitoring platform 400 includes a server system 410, a data store 430, wearable computing devices 402a, 402b, and 402c, external computing device 404, and a network 406. The wearable computing devices 402a, 402b, and 402c may have characteristics similar to those described above with respect to wearable computing device 302 in FIG. 3, where each wearable computing device is associated with a respective user 403a, 403b, and 403c. For example, each wearable computing devices 402a, 402b, and 402c, may be worn and/or used by a respective user 403a, 403b, and 403c. The network 406 may have characteristics similar to those described above with respect to network 306 in FIG. 3. The example external computing device 404 (e.g., a tablet, a smart phone, a laptop computer, etc.) may have characteristics similar to those described above with respect to external computing device 304 in FIG. 3. The data store 430 may be may be a memory (e.g., a random access memory, such as dynamic RAM (DRAM), static RAM (SRAM), double-data rate (DDR) RAM), a cache, a drive (e.g., a hard drive, a solid-state drive, a hybrid drive, magnetic disk drive, flash memory device), non-volatile memory devices, a database system, or another type of component/device capable of storing and/or accessing data. The data store 430 may also include multiple storage components (e.g., multiple drives or multiple databases) that may also span multiple computing devices (e.g., multiple server computers).

In some embodiments, one or more wearable computing devices (such as wearable computing device 402a) are directly connected to network 406. This may allow the one or more wearable computing devices to communicate (e.g., transmit/receive data) with the server system 410 and/or one or more external computing devices (such as external computing device 404). Multiple computing devices (including the external computing device 404) may be interconnected in a local area network (LAN) 407 (or another type of communication interconnection), which is connected to the network 406. The example LAN 407 may interconnect multiple computing devices, as well as one or more wearable computing devices such as 402b. In some implementations, one or more wearable computing devices such as wearable computing device 402b are connected to network 406, indirectly (e.g., through LAN 407 to one or external computing device 404 which is connected to the network 406). In some implementations, one or more wearable computing devices such as wearable computing device 402b are connected to network 406 directly, and indirectly through LAN 604, as described above. For example, wearable computing device 402b may be connected to external computing device 404 through a Bluetooth connection and external computing device 404 may be connected to server system 608 through network 406, and wearable computing device 402b may be connected to server system 608 through network 406.

The health/activity monitoring platform 400 may implement the server system 410 to collect detected physiological data, behavioral data, and/or environmental data from one or more wearable computing devices such as devices 402a, 402b and 402c as shown. For example, wearable computing device 402a may transmit collected physiological data and/or environmental data to server system 410. In another example, wearable computing device 402b may transmit collected physiological data and/or environmental data to the external computing device 404 and the external computing device 404 may transmit the physiological, behavioral data, and/or environmental data to the server system 410.

In some implementations, server system 410 is implemented on one or more standalone data processing apparatuses or a distributed network of computers. In some embodiments, server system 410 also employs various virtual devices and/or services of third party service providers (e.g., third-party cloud service providers) to provide the underlying computing resources and/or infrastructure resources of server system 410. In some embodiments, server system 410 includes, but is not limited to, a handheld computer, a tablet computer, a laptop computer, a desktop computer, a rackmount server, or a combination of any two or more computing devices.

As discussed above, the health/activity monitoring platform 400 may present health related messages to the users of the health/activity monitoring platform 400. For example, a message may include motivational messages (e.g., to encourage a user), status messages (e.g., about a user's current progress in meeting a health/fitness goal), informational messages (e.g., information and/or tips about health related topics), recommendation messages (e.g., recommended goals, recommend actions a user should take/perform, etc.). The health/activity monitoring platform 400 may identify and/or select messages to present to the users based on data collected about the users, as discussed in more detail below.

In one embodiment, the message module 420 may receive physiological data from one or more electronic devices. The physiological data may be generated by physiological sensors of the one or more electronic devices. For example, the physiological data may be generated by a heart rate sensor of wearable computing device 402b. The physiological data may be associated with a user. For example, the physiological data may be collected from the user 403b (e.g., may be associated with the user 403b). In some embodiments, the message module 420 may also receive environmental data (generated by sensors of the one or more electronic devices) and/or behavioral data (received from various computing devices and/or sensors). The message module 420 may identify a set of messages (e.g., insights, content, etc.) based on one or more of the physiological data, environmental data, and behavioral data. For example, the message module 420 may identify an initial set of messages related to a user's sleep based on one or more of the physiological data, environmental data, and behavioral data.

In one embodiment, the message module 420 may identify the set of messages based on user feedback that was submitted by one or more users of the health/activity monitoring platform 400. For example, users 403a, 403b, and/or 403c may be presented with messages from the health/activity monitoring platform 400. The users 403a, 403b, and/or 403c may provide feedback indicating whether the messages were useful, helpful, accurate, liked, etc. For example, user 403a may provide feedback indicating that a message was not helpful. In another example, user 403b may provide feedback indicating that a message was liked (e.g., that user 403b liked the content of the message). The message module 420 may identify other messages that have similar content, similar subject matter, etc., to the first message when user feedback for the first message is favorable (e.g., one or more users found the message useful, helpful, accurate, etc.). The message module 420 may also identify other messages that were presented to other users who are similar to a first user. For example, if the message module 420 is identifying messages to present to user 403b, the message module 420 may identify messages that were presented to user 403c because user 403b is similar to user 403c (e.g., user 403b and 403c have similar user preferences, have similar demographic information, have similar behavior, have similar physiological data, performed similar physical activities, etc.).

In one embodiment, message module 420 may identify the set of messages based on user preferences of the user. For example, if the user preferences of user 403b indicate that the user prefers to sleep later in the evening, then the messages that provide information about the pros/cons of sleeping late, may be presented to the user. The user preferences (for a particular user) may be provided by a user (e.g., the user may indicate that they like to play basketball) and/or may be determined/generated by the health/activity monitoring platform 400 (e.g., the health/activity monitoring platform 400 may determine that the user is a runner based on physiological data collected by a wearable computing device).

In one embodiment, each message of the health/activity monitoring platform 400 may be associated with one or more subject matter identifiers. A subject matter identifier may be a value (e.g., alphanumeric value, text, a number, etc.) that may be used to indicate that the first message is relevant and/or related to a particular subject or subject matter. A subject matter identifier may also be referred to as a tag. The message module 420 may identify the set of messages based on the subject matter identifiers associated with the set of messages (e.g., the subject matter identifiers associated with each message in the set of messages). For example, the message module 420 may identify a message that may deal with the subject matter of health problems of how inadequate sleep may affect a user's health.

The message module 420 may determine a set of scores (e.g., a set of presentation scores) for the set of messages (that were identified based on one or more of the physiological data, environmental data, and behavioral data). For example, the message module 420 may determine (e.g., calculate, generate, obtain, etc.) a presentation score for each message in the set of messages based on a base score and a set of penalties associated with each message, as discussed in more detail below. Each presentation score may be indicative of whether a respective message should be presented to a user. For example, each presentation score may indicate a likelihood (e.g., a probability) that a respective message will be presented to the user (e.g., the higher the presentation score the more likely the message may be presented to the user). The message module 420 may identify a first message from the set of messages based on the set of presentation scores. For example, the message module 420 may identify the message that has the highest presentation score (e.g., the first message may have the highest presentation score). The message module 420 may cause the first message to be presented to a user via a display of a computing device (of the user). For example, the message module 420 may transmit the first message to wearable computing device 402b and/or to external computing device 404. The wearable computing device 402b and/or the external computing device 404 may display the first message on a display device (e.g., on a touch screen, a liquid crystal display (LCD), etc.).

In one embodiment, the message module 420 may also update a first set of penalties associated with the first message in response to causing the first message to be presented to the user. For example, the message module 420 may update one or more penalties associated with the first message after transmitting the first message to a computing device of the user. The set of penalties (associated with the first message) may include a recency penalty (e.g., a penalty that may decrease the likelihood that a message may be displayed multiple times over a shorter period of time), a repetition penalty (e.g., a penalty that may decrease the likelihood that a message may be displayed multiple times over a longer period of time), and one or more subject matter penalties (e.g., penalties that may decrease the likelihood that other messages with the same topic/subject matter may be presented to the user multiple times). The set of penalties may decrease the likelihood that that first message may be presented to the user again. For example, the set of penalties for the first message may lower the presentation score for the first message to decrease the likelihood that the first message may be presented to the user again, as discussed in more detail below. In one embodiment, the message module 420 may update the first set of penalties (associated with the first message) by increasing one or more of the recency penalty, the repetition penalty, and the one or more subject matter penalties (as discussed in more detail below).

In one embodiment, the message module 420 may also apply a multiplier to a base score of a message to increase the likelihood that the message will be presented to a user. For example, the message module 420 may analyze physiological data and may determine that the user recently achieved a health/fitness goal (e.g., slept at least 8 hours a day for 7 days). The message module may apply a multiplier to the base score of a congratulatory message to increase the likelihood that the congratulatory message will be the next message that is presented to the user. In another example, a multiplier may be applied to the base score for a message about healthy food/eating may be during meal times for a user (e.g., around breakfast time, lunch time, dinner time, etc.). The multipliers may also be applied based on events and/or triggers. For example, the multipliers may be applied when the user performs certain actions, meets certain health/fitness goals, etc. The events and/or triggers may be determined based on the physiological data, behavioral data, environmental data, user data, and/or feedback data for a user. In some embodiments, the multiplier may be applied temporarily. For example, the multiplier may be applied for a period of time and may not be applied after the period of time passes/elapses.

In one embodiment, the penalties may increase the likelihood that a message will be presented to a user. For example, the values of the penalties may become negative values (instead of positive values). This may increase the likelihood that a message may be presented to the user. For example, if a message has not been presented to the user for a longer period of time (e.g., for a year), the recency penalty for the message may continue to decrease based on a recency penalty decay rate (as discussed in more detail below), until the recency penalty has a negative value.

As discussed above, each message of the health/activity monitoring platform 400 may be associated with one or more subject matter identifiers (e.g., an alphanumeric value, a number, text, etc.). In one embodiment, the message module 420 may identify subject matter penalties for the first message based on the one or more subject matter identifiers associated with first message. For example, message module 420 may identify a subject matter penalty for each subject matter identifier associated with the first message. The message module 420 may update the subject matter penalty for each subject matter identifier associated with the first message to decrease the likelihood that another message with the same topic/subject matter will be presented to a user again.

In one embodiment, the message module 420 may determine whether a period of time has elapsed. For example, the message module 420 may determine whether a day has passed, an hour has passed, 30 minutes has passed, etc. If the period of time has elapsed, the message module 420 may decrease one or more of the recency penalty, the repetition penalty, and the one or more subject matter penalties (as discussed in more detail below). For example, the message module 420 may decrease the repetition penalty by an amount for each day that passes.

In one embodiment, the content of a message may be updated to include information based on physiological data, environmental data, and/or behavioral data associated with a user. For example, a message may congratulate user 403b on sleeping for at least a certain number of hours in the previous evening. The number of hours indicated in the message may be based on an analysis of the physiological data to determine the actual number of hours that the user slept.

In one embodiment, the message module 420 may update base scores and/or penalties for messages based on user feedback (received from one or more users). For example, if user feedback is received from user 403b indicating that a message is not helpful, the base score of the message may be updated to decrease the likelihood that the message may be presented to the user 403b and/or other users (e.g., user 403a and 403c). In another example, subject matter penalty for a topic/subject matter may be increased if the user provides feedback that the user does not like message about the topic/subject matter.

In one embodiment, the message module 420 may identify messages (to present to a user) based on prerequisite messages associated with the first message. A prerequisite message may be a message that should be presented to a user first, before a subsequent message may be presented to the user. For example, a first message may be related to a particular concept for circadian rhythm. The message module 420 may not identify the first message unless a previous message (e.g., a prerequisite message), which introduces the general concept of circadian rhythm, has already been presented to the user. If the previous message (e.g., the prerequisite message) has not been previously presented to the user, the message module 420 may not present the first message to the user.

In one embodiment, prerequisite messages may be used to define a curriculum of messages. For example, prerequisite messages may be defined in order to cause the message module 420 to present the messages in the curriculum in a certain order. For example, a first message may be a prerequisite message for a second message, the second message may be a prerequisite message for a third message, the third message may be a prerequisite message for a fourth message, and the fourth message may be a prerequisite message for a fifth message. This may cause the message module 420 to present the first message before the second message, present the second message before the third message, present the third message before the fourth message, and present the fourth message before the fifth message. The curriculum of message may be useful when educating/teaching a user about a particular subject matter.

In one embodiment, the message module 420 may not present a first message that was previously presented to a user until a threshold number of messages were presented to the user after first message was previously presented. For example, the message module 420 may not present the first message to the user until at least five, ten, fifty, etc., messages were presented to the user after the first message was initially presented to the user.

As discussed above, the message module 420 may periodically identify sets of messages, determine sets of presentation scores (e.g., sets of scores) for the sets of messages, identify messages to present to a user, and cause the messages to be presented to the user. In one embodiment, the message module 420 may not present any messages to a user if there are no messages that are above a threshold score. For example, the message module 420 may identify a set of messages and determine a set of presentation scores for the set of messages. The message module 420 may determine that the highest presentation score (from the set of presentation scores) is less than a threshold score. The message module 420 may refrain from presenting any messages to a user In one embodiment, the message module 420 may not present a message to a user for a period of time after the message was previously presented to the user. For example, if a first message is presented to the user, the message module 420 may not present the first message to the user again until a period of time (e.g., a week, a month, a year, etc.) has elapsed. The period of time before the message module 420 may present the first message to the user again may be referred to as blackout period.

As discussed above, the health/activity monitoring platform 400 includes data store 430. The data store 430 may store physiological data 421, behavioral data 422, environmental data 423, user data 424, and message data 425. The health/activity monitoring platform 400 may identify messages (e.g., set of messages), determine presentation scores for messages, select messages (to present to users), and update scores/penalties, based on the physiological data 421, the behavioral data 422, the environmental data 423, the user data 424, and the message data 425, as discussed in more detail below.

In one embodiment, physiological data 421 may be data indicating the activity, physiological characteristics, and/or physiological state of one or more users of the health/activity monitoring platform 400. The physiological data 421 may be collected and/or obtained by various sensors in the computing devices of the users of the health/activity monitoring platform 400 (e.g., sensors in the wearable computing devices 402a, 402b, and/or 402c). Examples of physiological data 421 may include, but are not limited to, movement of the user, total sleep duration, total deep sleep duration, duration of wake time after sleep onset, total random-eye-movement (REM) sleep duration, breathing patterns of the user, temperature of the user, a number of waking events, timings of the waking events, sleep apnea, accumulated sleep debt, a maximum heart rate, a resting heart rate, a sleeping heart rate, heart-rate variability, a cardio fitness level, daily step data, an exercise type, an exercise duration, an exercise intensity, an exercise frequency, a running pace, a walking pace, active minutes data, sedentary time, length of longest sedentary periods, blood pressure, blood glucose level, an anaerobic threshold, and a cholesterol level.

In one embodiment, behavioral data 422 may be data indicating the behavior of one or more users of the health/activity monitoring platform 400. The behavioral data 422 may be collected and/or obtained by various computing devices and/or sensors. For example, the behavioral data 422 (e.g., where a user may go during different times of the day) may be collected by a GPS sensor of an external computing device of the user. In another example, a laptop computer may determine who the user has social interactions with (e.g., may determine who users chats with). Examples of behavioral data may include, but are not limited to, when a user performs certain actions (e.g., time of day), where the user performs certain actions (e.g., at home, at work, at a park, etc.), how the user may perform actions (e.g., an order in which the user may perform a series of actions), social connections of the user (e.g., the user's family, friends, etc.), who the user interacts with (e.g., who the user chats/talks to), etc.

In one embodiment, environmental data 423 may be data indicating environmental conditions for an environment of one or more user of the health/activity monitoring platform 400. The environmental data 423 may be collected and/or obtained by may be collected and/or obtained by various sensors in the computing devices of the users of the health/activity monitoring platform 400 (e.g., sensors in the wearable computing devices 402a, 402b, and/or 402c, external computing device 404, a game console, a thermostat, a camera, a microphone, a smart television, etc.). Examples of environmental data 423 may include, but are not limited to, temperature (e.g., a temperature of a room where a user is located), sound level (e.g., a noise level), humidity (e.g., humidity in an area where a user is located), air quality (e.g., a pollen/allergen count in an area where a user is located), lighting level (e.g., the amount of light in an area where a user is located, the color of the light in an area where a user is located) etc.

In one embodiment, user data 424 may be data indicating preferences and/or demographic information about the user. Some of the user data 424 may be provided by a user when the user joins (e.g., enrolls in, participates in, signs up for, etc.) the health/activity monitoring platform 400. For example, the user may provide demographic information (e.g., age, height, weight, sex, ethnicity, mailing address, etc.) when the user joins the health/activity monitoring platform 400. In another example, the user may indicate additional information about himself/herself such as their health, fitness, and/or activity goals, type of exercises/activities the user may engage in (e.g., running, cycling, swimming, basketball, etc.), when the user joins the health/activity monitoring platform 400. Some of the user data 424 may be determined by the health/activity monitoring platform 400 based on one or more of the physiological data 421, behavioral data 422, environmental data 423, and feedback data 425. For example, the health/activity monitoring platform 400 (e.g., the server system 410 and/or other server computers) may determine that the user 403a is a runner based on the movement of the user (detected by wearable computing device 402a), the user's heart-rate, and the temperature of the surroundings of user 403a (e.g., the outside temperature). Preferences that are determined by the health/activity monitoring platform 400 may be referred to as estimated preferences. Examples of user data 424 may include, but are not limited to, demographic information (e.g., age, sex, height, weight, ethnicity, etc.), user preferences (when the user prefers to sleep, whether the user is an early or late sleeper, etc.), user exercises/activities, user goals (e.g., fitness/health goals, such as target weight, a target distance to run/bike, a target time to perform an activity), etc.

In one embodiment, feedback data 425 may be data indicating whether users (e.g., user 403a, user 403b, and/or user 403c) liked or disliked messages that were presented by the health/activity monitoring platform 400. The feedback data 425 may be collected and/or obtained by computing devices, such as wearable computing devices 402a-402c, and external computing device 404. For example, user 403b may provide input (via a graphical user interface (GUI) displayed by external computing device 404 and/or wearable computing device 402b) indicating whether the user 403b liked/disliked a message that was presented to the user 403b (via external computing device 404 and/or wearable computing device 402b). Additional details regarding providing, receiving and/or analyzing feedback provided by users of the health/activity monitoring platform 400 are discussed in more detail below.

In one embodiment, the message data 426 may include data indicating penalties, penalty decays (e.g., the rate at which a penalty decrease), subject matter identifiers, scores (e.g., a base score, a presentation score, etc.), prerequisites, identifiers for messages (e.g., names, identification numbers/values, etc.). For example, the message data 426 may indicate an identifier (e.g., a name) for a message, a recency penalty for the message, a repetition penalty for the message, a recency penalty decay rate, one or more subject matter identifiers (e.g., tags) for the message, a base score for the message, and the presentation score (e.g., a score determined, calculated, and/or generated based on the base scores and one or more penalties).

In another embodiment, the message data 426 may also include data indicating subject matter penalties for subject matter identifiers. As discussed above, each message may be associated with one or more subject matter identifiers and subject matter identifiers may indicate the message is related to a particular subject matter (e.g., circadian rhythm, sleep debt/deficit, etc.). Each subject matter identifier may be associated with a subject matter penalty. The subject matter penalty (for a subject matter identifier) may be updated each time a message that is associated with the subject matter identifier is presented to a user. When a message that is associated with multiple subject matter identifiers is presented to a user, multiple subject matter penalties may be updated.

In a further embodiment, the message data 426 may also include the content (or portions of the content) of messages that may be presented to a user. For example, the message data 426 may include text, images, video, icons, symbols, etc., that may be included in the message when the message is displayed/presented to the user. As discussed above, the content (or portions of content) of the messages may be updated to include information based on physiological data, environmental data, and/or behavioral data associated with a user. For example, the message data 426 may include a template message that congratulates the user on achieving a goal (e.g., sleeping more than 7 hours a night). Portions of the template message (e.g., the congratulatory message) may be replaced with actual number of hours the user slept, based on the physiological data collected for the user.

Although the messages, topics/subject matters, physiological data, behavioral data, environmental data, user data, and feedback data described herein may refer to a user's sleep, one having ordinary skill in the art understands that the examples, implementations, and/or embodiments described herein may be applied to other types of health related concepts. For example, the messages and topics/subject matters may be related to physical activities/exercises. In another example, the messages and topics/subject matters may be related to a user's diet or eating habits.

Figure 5:
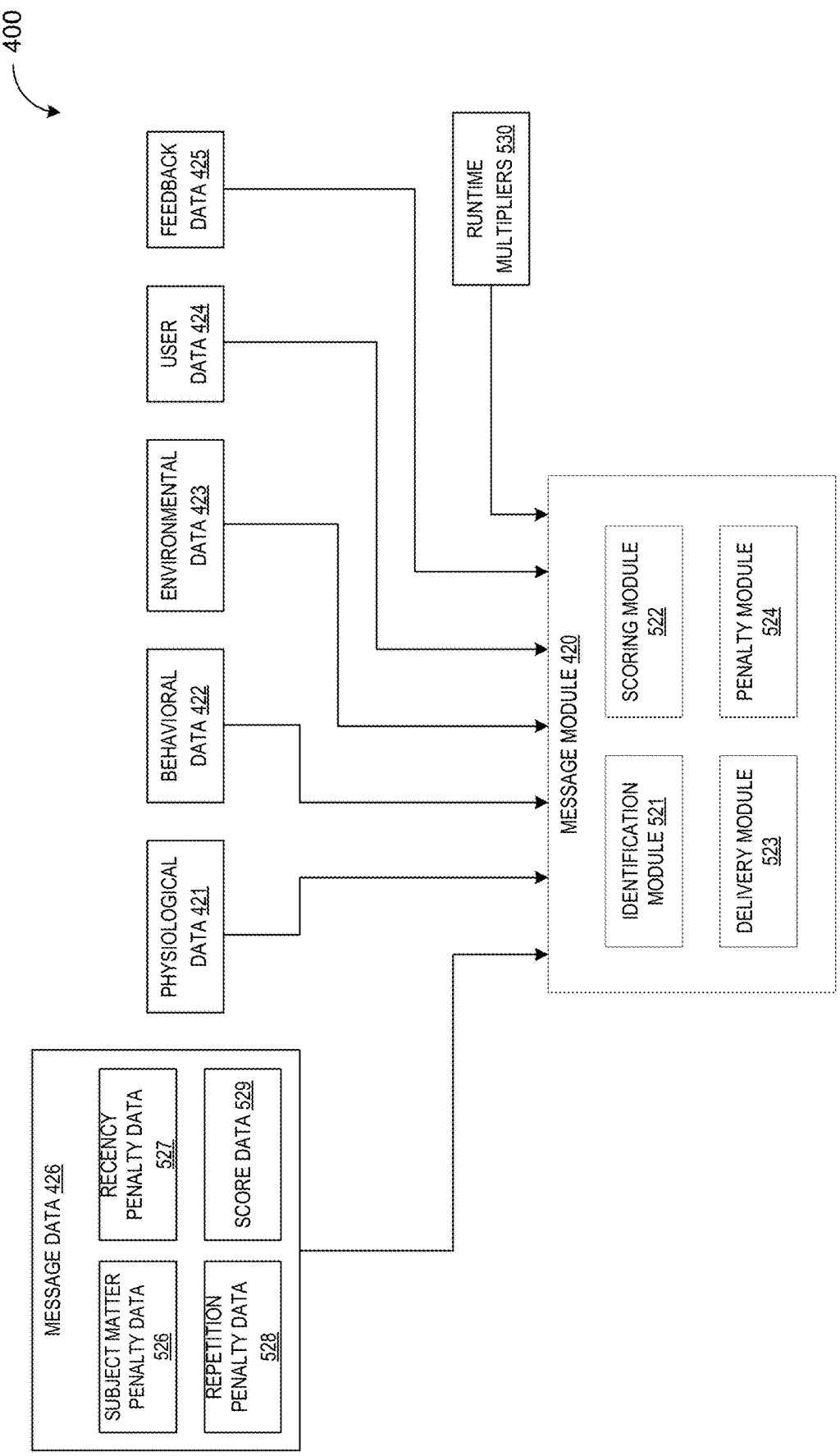
FIG. 5 illustrates a message module, in accordance with one or more embodiments.

FIG. 5 illustrates a message module 420, in accordance with one or more embodiments. The message module 420 includes an identification module 521, a scoring module 522, a delivery module 523, and a penalty module 524. More or less components may be included in the message module 420 without loss of generality. For example, two of the modules may be combined into a single module, or one of the modules may be divided into two or more modules. In one embodiment, one or more of the modules may reside on different computing devices (e.g., different server computers/systems). The identification module 521, the scoring module 522, the delivery module 523, and the penalty module 524 may each be processing logic that comprises hardware (e.g., circuitry, dedicated logic, programmable logic, microcode, etc.), software (e.g., instructions run on a processor to perform hardware simulation), or a combination thereof. The message module 420 may be part of a health/activity monitoring platform (as discussed above in conjunction with FIG. 4).

As discussed above, physiological data 421 may be data indicating the activity, physiological characteristics, and/or physiological state of one or more users of the health/activity monitoring platform. Also as discussed above, behavioral data 422 may be data indicating behaviors of a user. Environmental data 423 may be data indicating environmental conditions for an environment of one or more user of the health/activity monitoring platform, as discussed above. User data 424 may be data indicating preferences of a user, as discussed above. Feedback data 425 may be data indicating whether users liked or disliked messages that were presented to the users, as discussed above.

The message data 426 includes subject matter penalty data 526 which may indicate the subject matter penalties for all of the different subject matters of the messages. As discussed above, each message may be related to one or more subject matters and the one or more subject matters are identified by subject matter identifiers (e.g., tags, alphanumeric values, etc.). Each time a message that is related to a subject matter is presented to a user, the subject matter penalty for the subject matter is updated to decrease the likelihood that another message related to the same subject matter will be presented to the user. For example, the value of the subject matter penalty for the subject matter may be increased. Different subject matter penalties (for different subject matters) may have different initial values (e.g., different starting values, such as 0, 0.1, 0.3, etc.). In addition, different subject matter penalties (for different subject matters) may be updated (e.g., increased/decreased) by different amounts (e.g., 0.05, 0.1, etc.).

In some embodiments, the subject matter penalties may be adjusted and/or updated. For example, if a user has indicated that they like messages that are related to the subject of sleep debt, the subject matter penalty for the subject of sleep debt may be decreased because the message module 420 may want to present more messages related to the subject of sleep debt to the user more often. Decreasing the value/amount of a subject matter penalty (e.g., decreasing the subject matter penalty from 0.1 to 0.05) may increase the likelihood that messages related to the subject of sleep debt may be presented to the user. The subject matter penalties may be adjusted/updated by the message module 420 (e.g., may be updated automatically by the message module 420 based on one or more of the physiological data 421, behavioral data 422, environmental data 423, user data 424, and feedback data 425), or may be adjusted/updated by an administrative user (e.g., an administrator) of the health/activity monitoring platform.

The subject matter penalty data 526 may also include penalty decay rates (e.g., subject matter penalty decay rates) for the different subject matter penalties. Furthermore, the subject matter penalty decay rates (e.g., the rate at which the subject matter penalty is decreased) may be different for different subject matters. For example, a first subject matter (e.g., circadian rhythm) may have a faster subject matter penalty decay rate (e.g., may decrease faster) than a second subject matter (e.g., sleep debt). The penalty decay rates may be linear, may be exponential, may be based on a function/equation, etc.

In some embodiments, the subject matter penalty decay rates may be adjusted and/or updated. For example, if a user has indicated that the user does not like messages about sleep debt, the subject matter penalty decay rate for the subject of sleep debt may be decreased because the message module 420 may want present fewer messages related to the subject of sleep debt to the user. Decreasing the value/amount of the subject matter penalty decay rate (e.g., decreasing the subject matter penalty decay rate from 0.1 per day to 0.05 per day) may decrease the likelihood that messages related to the subject of sleep debt may be presented to the user. The subject matter penalty decay rates may be adjusted/updated by the message module 420 (e.g., may be updated automatically by the message module 420 based on one or more of the physiological data 421, behavioral data 422, environmental data 423, user data 424, and feedback data 425), or may be adjusted/updated by an administrative user (e.g., an administrator) of the health/activity monitoring platform.

TABLE 1

| Subject Matter Identifier | Subject Matter Penalty (Per/Current) | Subject Matter Penalty Decay Rate |
| --- | --- | --- |
| Circadian Rhythm | 0.1/0.4 | 0.1 per day |
| Consistency | 0.02/0.08 | 0.01 per 2 days |
| . . . | . . . | . . . |
| Sleep Debt | 0.015/0.045 | 0.02 every week |
| Sleep Duration | 0.2/0 | 0.1 every 2 weeks |
| Sleep Goal | 0.08/0.13 | 0.03 every 5 days |

In one embodiment, portions of the message data 426 (which may include the subject matter penalty data 526) may be represented using a table. Table 1 (shown above) illustrates an example message data that may be represented using a table. The table includes three columns. The first column of Table 1 (Subject Matter Identifier) represents the name or identifier for topic and/or subject matter of one or more messages of the health/activity monitoring platform. For example, Sleep Goal is an identifier for a topic/subject matter for one or more messages of the health/activity monitoring platform. The second column of Table 1 (Subject Matter Penalty) represents the subject matter penalty that may be that may be added to the current subject matter penalty when a message associated with the respective subject matter identifier is presented to a user. For example, if a message that is associated with the subject matter identifier Sleep Debt is presented to a user, the subject matter penalty of 0.015 may be added to the current subject matter penalty of 0.045 for the Sleep Debt subject matter. The third column of Table 1 represents the subject matter penalty decay rate for a topic/subject matter. For example, the subject matter penalty decay rate for subject matter Sleep Goal is 0.03 every 5 days (e.g., the subject matter penalty for the subject matter Sleep Goal will decrease by 0.03 every 5 days).

In one embodiment, the message data 426 may include a different set of subject matter penalties for each user of the health/activity monitoring platform. For example, the message data 426 may include multiple tables (e.g., multiple instances of Table 1), one table for each user of the health/activity monitoring platform. Different users may be presented with messages related to different topics/subject matters based on physiological data, behavioral data, environmental data, user data, and feedback data collected for each user. This may allow the message module 420 to track the scores and penalties for the message of the health/activity monitoring platform on an individual user basis because different users may be presented with different messages.

The message data 426 also includes recency penalty data 527 which may indicate recency penalties for messages that have been recently presented to a user. The recency penalties may reduce the likelihood that a message may be presented multiple times to a user within shorter time period or time frame. For example, a recency penalty may reduce the likelihood that a message will be presented twice to a user within the same day, week, 2 weeks, etc. Each message (that may be presented by the health/activity monitoring platform) may have a respective recency penalty. Each time a message is presented to a user, the recency penalty for the message may be increased by a value/amount (e.g., the recency penalty may be increased by 1, 0.6, 0.25, etc.). Different recency penalties (for different messages) may have different initial values (e.g., different starting values, such as 0.5, 0.3, etc.). In addition, different subject matter penalties (for different subject matters) may be updated (e.g., increased/decreased) by different amounts (e.g., 0.05, 0.1, etc.).

In some embodiments, the recency penalties may be adjusted and/or updated. For example, if a user is constantly achieving/meeting a health/fitness goal (e.g., is constantly sleeping more than goal of 7 hours per night), the recency penalty for a congratulatory message may be decreased because the message module 420 may want present the congratulatory message to the user more often (to encourage or motivate the user). Decreasing the value/amount of recency penalty (e.g., decreasing the recency penalty from 0.5 to 0.1) may increase the likelihood that the congratulatory message may be presented to the user. The recency penalties may be adjusted/updated by the message module 420 (e.g., may be updated automatically by the message module 420 based on one or more of the physiological data 421, behavioral data 422, environmental data 423, user data 424, and feedback data 425), or may be adjusted/updated by an administrative user (e.g., an administrator) of the health/activity monitoring platform.

The recency penalty data 527 may also include decay rates for the recency penalties (for messages that have been recently presented to a user). For example, the recency penalty data 527 may indicate that a recency penalty for a first message may decrease at a rate of 0.01 per day. The decay rate for a recency penalty may indicate the rate at which the recency penalty will decrease. For example, the decay rate may indicate the amount (or value) by which the recency penalty should be decreased per period of time (e.g., per hour, per day, per week, etc.).

In some embodiments, the recency penalty decay rates may be adjusted and/or updated. For example, if the message module 420 determines that a user is constantly sleeping at least a threshold number of hours per night (e.g., at least seven hours), the recency penalty decay rate for a message that congratulates the user for sleeping enough (e.g., a congratulatory message) may be decreased. Decreasing the value/amount of the recency penalty decay rate (e.g., decreasing the recency penalty decay rate from 0.1 per day to 0.05 per day) may decrease the likelihood the congratulatory message may be presented multiple times to the user within a time period or time frame. The recency penalty decay rates may be adjusted/updated by the message module 420 (e.g., may be updated automatically by the message module 420 based on one or more of the physiological data 421, behavioral data 422, environmental data 423, user data 424, and feedback data 425), or may be adjusted/updated by an administrative user (e.g., an administrator) of the health/activity monitoring platform.

The message data 425 further includes repetition penalty data 528 which may indicate repetition penalties for messages that have been previously presented to a user. The repetition penalties may reduce the likelihood that a message may be presented multiple times to a user within longer time period or time frame. For example, a repetition penalty may reduce the likelihood that a message will be presented multiple times to a user within a few months, a year, etc. Each message (that may be presented by the health/activity monitoring platform) may have a respective repetition penalty. Each time a message is presented to a user, the repetition penalty for the message may be increased by a value/amount (e.g., the repetition penalty may be increased by 0.05, 0.075, etc.). Different repetition penalties (for different messages) may have different initial values (e.g., different starting values). In addition, different subject matter penalties (for different subject matters) may be updated (e.g., increased/decreased) by different amounts.

In one embodiment, the repetition penalties may not have a decay rate (e.g., the repetition penalties may not be decreased over time). When a repetition penalty for a message is not decreased over time, this may cause the likelihood that the message will be presented again to a user to continually decrease each time the message is presented to the user. The repetition penalties may allow the message module 420 to increase the likelihood that different and/or new message will be presented to the user over a longer period of time by decreasing the likelihood that previously presented messages will be present to the user. In an alternative embodiment, a repetition penalty may also have a decay rate (e.g., a repetition penalty decay rate). The repetition penalty decay rate may be similar to the recency penalty decay rates. However, the decay rate for a repetition penalty may be lower/smaller than the recency penalty decay rates.

The message data 425 further includes score data 529 which may include data indicating scores for each message. In one embodiment, the score data 529 may indicate base scores for the messages of the health/activity monitoring platform. The base score may be an initial score that is used to calculate, generate, determine, etc., a presentation score for the message. A higher base score may increase the likelihood that a message is presented to the user, and vice versa. The score data 529 may be updated when the base score for a message is updated/changed (as discussed above). In another embodiment, the score data 529 may also indicate presentation scores for the messages of the health/activity monitoring platform. For example, a presentation score for a message may be calculated, generated, determined, etc., using a base score for the message and one or more penalties for the message (e.g., a recency penalty, a repetition penalty, one or more subject matter penalties, etc.). The presentation score for a message may be stored in the score data 529 each time the presentation score is calculated, generated, determined, etc. The score data 529 may be updated each time the presentation score is calculated, generated, determined, etc.

TABLE 2

| Message ID | Base Score | Recency Penalty (Per/Current) | Recency Penalty Decay Rate | Repetition Penalty (Per/Current) | Presentation Score | Blackout Period | Subject Matter Identifier | Prerequisites |
|---|---|---|---|---|---|---|---|---|
| CR_1 | 1.5 | 0.5/0.7 | 0.1 per week | 0.01/0.1 | 1.2 | | Circadian Rhythm | |
| CR_2 | 1.0 | 0.2/0.1 | 0.05 per day | 0.05/0.45 | 0.75 | 1 week | Circadian Rhythm, Consistency | CR_1 |
| CR_3 | 1.0 | 0.2/0.3 | 0.05 per day | 0.025/0.2 | 0.8 | 1 week | Circadian Rhythm, Consistency | CR_1, CR_2 |
| SD_1 | 0.9 | 0.2/0.4 | 0.1 per day | 0.01/0.3 | 0.66 | 2 days | Sleep Debt | |
| ... | ... | ... | ... | ... | ... | ... | ... | ... |
| GOAL_8 | 1.2 | 0.1/0.9 | 0.2 per week | 0.1/0.12 | 1.2 | | Sleep Duration, Sleep Goal | |

In one embodiment, portions of the message data 426 (which may include the subject matter penalty data 526, the recency penalty data 527, the repetition penalty data 528, and the score data 529) may be represented using a table. Table 2 (shown above) illustrates an example message data that may be represented using a table. The table includes nine columns. The first column of Table 2 (Message ID) represents the name or identifier for a message. For example, CR_1 is an identifier for a first message, CR_2 is an identifier for a second message, etc. The second column (Base Score) represents the base score for a message. For example, the message CR_3 has a base score of 1.0.

The third column of Table 2 (Recency Penalty) represents the recency penalty that should be applied to a current value of the recency penalty when the message is presented to the user. For example, if the message SD_1 is presented to the user, a recency penalty of 0.2 should be added to the current recency penalty of 0.4. The current recency penalty may be applied to the presentation score for message SD_1 when the presentation score is calculated. The fourth column of Table 2 (Recency Penalty Decay Rate) represents the recency penalty decay rate for a message. For example, the recency penalty decay rate for the message GOAL_8 is 0.2 per week (e.g., the recency penalty will decrease by 0.2 every week.

The fifth column of Table 2 (Repetition Penalty) represents the repetition penalty that should be applied to a current value of the repetition penalty when the message is presented to the user. For example, if the message SD_1 is presented to the user, a repetition penalty of 0.1 should be added to the current repetition penalty of 0.3. The current repetition penalty may be applied to the presentation score for message SD_1 when the presentation score is calculated.

The sixth column of table 2 (Presentation Score) represents the presentation score of a message. For example, message CR_2 has a presentation score of 0.75. As discussed above, presentation score may be calculated, generated, determined, etc., by the message module 420. The presentation score for a message may be calculated based on the base score for the message, the recency penalty, the repetition penalty, and one or more subject matter penalties (which may be determined using subject matter identifiers) for the message. One having ordinary skill in the art understands that the presentation score for a message may be calculated, determined, generated, etc., using various methods, formulas, equations, functions, operations, algorithms, etc. Examples of equations/formulas that may be used to calculate a presentation score for a message are discussed in more detail below in conjunction with equations (1)-(7).

The seventh column of Table 2 (Blackout Period) represents a blackout period for a message. A blackout period may be a minimum amount of time that should elapse after a message is presented to a user, before the message module 420 may allow a message to be presented to the user again. For example, message SD_1 has a blackout period of 2 days. This may indicate that message SD_1 cannot be presented to the user until at least 2 days after the message SD_1 was previously presented.

The eight column of Table 2 (Subject Matter Identifier) represents subject matter identifiers for a message. As discussed above, a subject matter identifier may identify a topic/subject matter of a message. For example, the subject matter identifier Sleep Debt may indicate that the message is related to the subject of sleep debt (e.g., the cumulative effect of not getting enough sleep). Subject matter penalties may be identified based on one or more subject matter identifiers for a message. For example, message CR_2 has subject matter identifiers Circadian Rhythm and Consistency (e.g., subject matter related to how to establish consistent sleeping habits). The subject matter penalties for Circadian Rhythm and Consistency may be identified using Table 1 and may be used when calculating the presentation score for message CR_2.

The ninth column of Table 2 (Prerequisites) represents prerequisite messages for a message. As discussed above, a prerequisite message for a message may be a previous message that should be presented to a user for the current message may be presented to the user. For example, message CR_2 may not be presented to a user unless CR_1 has already been presented to the user (e.g., was previously presented to the user). In another example, message CR_3 may not be presented to the user unless both CR_1 and CR_2 have already been presented to the user.

In one embodiment, the message data 426 may include a set of scores and penalties for each user of the health/activity monitoring platform. For example, the message data 426 may include multiple tables (e.g., multiple instances of Table 2), one table for each user of the health/activity monitoring platform. Different users may be presented with different messages based on physiological data, behavioral data, environmental data, user data, and feedback data collected for each user. This may allow the message module 420 to track the scores and penalties for the message of the health/activity monitoring platform on an individual user basis because different users may be presented with different messages.

As discussed above, the message module 420 may identify messages that may possibly be presented to a user, based on one or more of the physiological data 421, behavioral data 422, environmental data 423, user data 424, and feedback data 425, collected for a user. For example, the health/activity monitoring platform may have thousands of messages that may be presented to users of the health/activity monitoring platform. The identification module 521 may analyze the physiological data 421, behavioral data 422, environmental data 423, user data 424, and feedback data 425 collected for the user to identify a subset of messages (e.g., twenty messages, fifty-six messages, etc., of the thousands of messages) that may be new, relevant, interesting, useful, etc., to the user.

In one embodiment, the identification module 521 may analyze one or more of the physiological data 421, behavioral data 422, environmental data 423, user data 424, and feedback data 425 to identify a set of messages from the pool of messages that are in the health/activity monitoring platform. For example, the identification module 521 may determine that a user is constantly waking up from sleep during the evenings, based on the physiological data collected for the user (which may be included in physiological data 421). The identification module 521 may identify messages that may be related to the subject matter of how to sleep through the evening uninterrupted. In another example, the identification module 521 may analyze the behavioral data and may determine that the user interacts with another user of the health/activity monitoring platform. The identification module 521 may identify messages that were also presented to the other user because the user and the other user may share similar interests. In a further example, the identification module 521 may analyze the environmental data collected for the user (which may be included in environmental data 423) and may determine that the temperature of the room where the user's sleeps is too warm. The identification module 521 may identify messages that may related to setting a room temperature to a temperature that is conducive to sleeping. In one example, the identification module 521 may analyze user data 424 and may determine that the user is a runner. The identification module 521 may identify messages that discuss how running may help a user achieve more restful sleep if the user runs closer to their bedtime. In another example, the identification module 521 may analyze feedback data 425 and may determine that a user has indicated that the user likes receiving messages suggesting additional goals (e.g., sleeping goals, fitness goals, exercise goals, etc.) for the user. The identification module 521 may identify messages that may be related to user goals based on the feedback data 425.

In one embodiment, the identification module 521 may identify sets of messages for a user (e.g., identify a set of messages for each user of the health/activity monitoring platform) periodically. For example, the identification module 521 may identify a set of messages for a user every day, every week, every five days, etc. In another example, the identification module 521 may identify a set of messages based on the time of day (e.g., every morning, every afternoon, etc.). In a further example, the identification module 521 identify sets of messages based on a schedule (which may be created by an administrator of the health/activity monitoring platform).

In another embodiment, the identification module 521 may analyze one or more of the physiological data, 421, the behavioral data 422, the environmental data 423, the user data 424, and the feedback data 425 to identify events and/or triggers that may cause the identification module 521 to identify a set of messages for the user. Examples of an event may include, but are not limited to, an action performed by a user, a goal that is achieved/met by a user, etc. Examples of a trigger may include, but are not limited to, receiving new physiological data, receiving new environmental data, receiving new user data, receiving new behavioral data, determining that a user has perform an action (e.g., a user has woken up or a user is going to sleep), determining that the user is accessing a health/fitness application, etc. When the identification module 521 identifies one or more events and/or triggers the identification module 521 may identify new messages to include in a set of messages for the user. For example, the identification module 521 may analyze the physiological data collected for a user and determine that a user was unable to sleep through the night without waking up in the middle of the night for five days in a row. This may cause the identification module 521 to identify messages that may be related to tips/advice for sleeping through the night without waking up (e.g., to identify new messages to include in the set of messages for the user).

In one embodiment, new messages (e.g., messages that were not in a previous set of messages) may be included in the current set of messages that are identified by the identification module 521 and messages that were in a previous set of messages may be removed from the current set of messages, when the identification module 521 identifies new sets of messages (periodically and/or based on events/triggers). This may allow the identification module 521 to continually present the user with new, interesting, and/or relevant messages (e.g., new, interesting, and/or relevant content).

In one embodiment, the scoring module 522 may determine a set of scores (e.g., a set of presentation scores) for the set of messages that is identified by the identification module 521. As discussed above, each message in the set of messages is associated with a base score, a recency penalty, a repetition penalty, and one or more subject matter penalties (as illustrated above in Table 2). The scoring module 522 may determine a presentation score for each message based on one or more of the respective base score, the respective recency penalty, the respective repetition penalty, the respective subject matter penalties for the message, and one or more multipliers (e.g., runtime multipliers that may be applied to the base score and/or one or more of the penalties for the message). The scoring module 522 may update the presentation scores for the messages (in the set of messages) in the score data 529/message data 426. For example, the scoring module may update the presentation scores in the messages for the copy/instance of Table 2 that is associated with the user.

As discussed above, the score module 522 may calculate, determine, generate, etc., the presentation score for a message using various methods, formulas, equations, functions, operations, algorithms, etc. Examples of equations, functions, and/or formulas that may be used by the scoring module 522 are illustrated below in equations (1)-(7). One having ordinary skill in the art understands that in other embodiments, different parameters/variables and operations (e.g., multiplication, subtract, addition, etc.) may be used in the formulas/equations for calculating the presentation score.

$$p_{score} = b_{score} \quad (1)$$

$$p_{score} = b_{score} * r_{multiplier} \quad (2)$$

$$p_{score} = b_{score} - (b_{score} * recency_{penalty}) \quad (3)$$

$$p_{score} = b_{score} - (b_{score} * recency_{penalty} * prod(sm_{penalty})) \quad (4)$$

$$p_{score} = (b_{score} * r_{multiplier}) - (b_{score} * recency_{penalty} * prod(sm_{penalty})) \quad (5)$$

$$p_{score} = (b_{score} * r_{multiplier}) - ((b_{score} * recency_{penalty} * prod(sm_{penalty})) + repetition_{penalty}) \quad (6)$$

$$p_{score} = b_{score} - recency_{penalty} - sum(sm_{penalty}) - repetition_{penalty} \quad (7)$$

Equation (1) illustrates a first example equation that may be used by the scoring module 522 to determine (e.g., calculate) a presentation score ($p_{score}$) for a message based on a base score for the message ($b_{score}$). Equation (2) illustrates a second example equation that may be used by the scoring module 522 to determine a presentation score based on the base score ($b_{score}$) and a runtime multiplier ($r_{multiplier}$). As discussed above, a runtime multiplier may be applied to a base score (e.g., may be multiplied to, added to, etc.) a base score and/or a penalty to increase the likelihood that a message may be presented to a user. Equation (3) illustrates a third equation that may be used by the scoring module 522 to determine a presentation score for a message ($p_{score}$) based on the base score for the message ($b_{score}$) and a recency penalty for the message ($recency_{penalty}$). Equation (4) illustrates a third equation that may be used by the scoring module 522 to determine a presentation score for a message ($p_{score}$) based on the base score for the message ($b_{score}$), a recency penalty for the message ($recency_{penalty}$), and the product of all of the subject matter penalties for the message ($prod(sm_{penalty})$).

Equation (5) illustrates a third equation that may be used by the scoring module 522 to determine a presentation score for a message ($p_{score}$) based on the base score for the message ($b_{score}$), a runtime multiplier ($r_{multiplier}$), a recency penalty for the message ($recency_{penalty}$), and the product of all of the subject matter penalties for the message ($prod(sm_{penalty})$). Equation (6) illustrates a third equation that may be used by the scoring module 522 to determine a presentation score for a message ($p_{score}$) based on the base score for the message ($b_{score}$), a runtime multiplier ($r_{multiplier}$), a recency penalty for the message ($recency_{penalty}$), the product of all of the subject matter penalties for the message ($prod(sm_{penalty})$), and a repetition penalty for the message ($repetition_{penalty}$). Equation (7) illustrates a third equation that may be used by the scoring module 522 to determine a presentation score for a message ($p_{score}$) based on the base score for the message ($b_{score}$), a recency penalty for the message ($recency_{penalty}$), the sum of all of the subject matter penalties for the message ($sum(sm_{penalty})$), and a repetition penalty for the message ($repetition_{penalty}$).

In one embodiment, the scoring module 522 may determine scores (e.g., presentation scores) for a set of messages (identified by the identification module 521) periodically. For example, the scoring module 522 may determine scores for a set of messages for a user every hour, every day, every three days, etc. In another example, the scoring module 522 may determine scores for a set of messages for a user based on the time of day (e.g., every morning, every afternoon, etc.). In a further example, the scoring module 522 may determine scores for a set of messages for a user based on a schedule (which may be created by an administrator of the health/activity monitoring platform).

In another embodiment, the scoring module 522 may analyze one or more of the physiological data, 421, the behavioral data 422, the environmental data 423, the user data 424, and the feedback data 425 to identify events and/or triggers that may cause the scoring module 522 to determine scores (e.g., presentation scores) for a set of messages, as discussed above. When the scoring module 522 identifies one or more events and/or triggers the scoring module 522 may determine scores for a set of messages. For example, the scoring module 522 may determine a set of scores when a user access a health/fitness application (that helps the user monitor/track their health, physical activity, etc.) on their external computing device. The health/fitness application may transmit a message to the message module 420 (e.g., to the scoring module 522) when the health/fitness application is accessed/used by the user and the scoring module 522 may determine that a message (e.g., an insight, content, etc.) should be presented to the user and may determine scores for the set of messages to identify a message to present to the user.

As discussed above, the health/activity monitoring platform may track the scores and penalties for the message of the health/activity monitoring platform on an individual user basis because different users may be presented with different messages. For example, the message data (e.g., the subject matter penalty data 526, recency penalty data 527, repetition penalty data 528, and/or score data 529) may include an instance/copy of Table 1 and Table 2 for each user of the health/activity monitoring platform. In one embodiment, the penalty module 525 may adjust, modify, update, etc., penalties for the messages of the health/activity monitoring platform when a message is presented to a user. For example, when a message is presented to the user, the penalty module 525 may identify the copy of Table 1 and Table 2 that is associated with the user. The penalty module 525 may also identify the entries (e.g., rows) in Table 1 and Table 2 that corresponds to the message (e.g., may identify the entries based on the message identifier for the message). The penalty module 525 may update (e.g., increase) the recency penalty for the message (e.g., may update the recency penalty in the entry for the message in Table 2), as discussed above. The penalty module 525 may also update (e.g., increase) the repetition penalty for the message (e.g., may update the repetition penalty in the entry for the message in Table 2), as discussed above. The penalty module 525 may also update the subject matter penalties for the topics/subject matters of the messages. For example, as discussed above each message may be associated with subject matter identifiers that identify the topics/subject matters of the message. The penalty module 525 may identify the topics/subject matters of the message, in the copy of Table 1 that is associated with the user. The penalty module 525 may update (e.g., increase) the subject matter penalties for each of the topics/subject matters of the message in the copy of Table 1 that is associated with the user.

In another embodiment, the penalty module 525 may adjust, modify, update, etc., penalties for the messages of the health/activity monitoring platform on an individual user basis (as discussed above), based on penalty decay rates for the different penalties. The penalty module 525 may adjust, modify, update, etc., the penalties for the messages periodically. For example, the penalty module 525 may update the penalties for each of the messages every hour, every six hours, every day, etc., based on a respective penalty decay rate for the penalty. The penalty module 525 may identify/determine the decay rate for a penalty for a message, and may decrease the penalty by the decay rate based on the amount of time that has elapsed since the last time the penalty was decreased (e.g., decayed). For example, referring to Table 2, if one week has passed since the last time the penalty module 525 decreased (e.g., decayed) the recency penalty for message CR_1, the penalty module 525 may decrease the recency penalty by 0.1 (e.g., decrease the recency penalty from 0.7 to 0.6). In another example, referring to Table 1, if 12 hours has passed since the last time the penalty module 525 decreased (e.g., decayed) the subject matter penalty for the subject matter Circadian Rhythm, the penalty module 525 may decrease the subject matter penalty by 0.05.

In one embodiment, the delivery module 523 may cause the message that is identified by the scoring module 522 to be presented to a user. For example, the delivery module 523 may transmit the message to an external computing device (e.g., a smartphone, a tablet, etc.) of the user. In another example, the delivery module 523 may transmit the message to a wearable computing device of the user.

Although the messages, topics/subject matters, physiological data, behavioral data, environmental data, user data, and feedback data described herein may refer to a user's sleep, one having ordinary skill in the art understands that the examples, implementations, and/or embodiments described herein may be applied to other types of health related concepts. For example, the messages and topics/subject matters may be related to physical activities/exercises. In another example, the messages and topics/subject matters may be related to a user's diet or eating habits.

FIG. 6A is a graph 610 that illustrates changes to a recency penalty over time in accordance with one or more embodiments. The x-axis of the graph 610 represents time, ranging from 0 to T_X. The y-axis of the graph 610 represents the value of the recency penalty, ranging from 0 to 1. As discussed above, the recency penalty may be for a particular message for a user in a health/activity monitoring platform. As illustrated in graph 610, the recency penalty may start at the value 0 until time T1. At time T1, the message may be presented to the user and the recency penalty for the message may be increased to 0.75. The recency penalty may decrease (e.g., decay) at a penalty decay rate (e.g., at a recency penalty decay rate for the particular message) between time T1 and T2. At time T2, the message may be presented to the user for a second time and the recency penalty may be increased by 0.75 to approximately 0.875. The recency penalty may decrease (e.g., decay) at the penalty decay rate (e.g., at the recency penalty decay rate) between time T2 and T3. At time T3, the message may be presented to the user for a third time and the recency penalty may be increased to 1.0.

FIG. 6B is a graph 620 that illustrates changes to a subject matter penalty over time in accordance with one or more embodiments. The x-axis of the graph 610 represents time, ranging from 0 to T_X. As discussed above, the subject matter penalty may be for a particular topic/subject matter for messages for a user in a health/activity monitoring platform. As illustrated in graph 620, the subject matter penalty may be increased when a message which has the particular subject matter is presented to the user. The subject matter penalty may decrease until the subject matter penalty reaches 0 or until another message which has the particular subject matter is presented to the user. For example, the subject matter penalty may start at the value 0 until time T1. At time T1, a message which has the particular subject matter may be presented to the user and the subject matter penalty for particular subject matter may be increased. The subject matter penalty may decrease (e.g., decay) at a penalty decay rate (e.g., at a subject matter penalty decay rate for the particular subject matter) between time T1 and T2, when another message with the particular subject matter is presented to the user. In another example, the subject matter penalty may decrease to 0 between time T8 and T9. The subject matter penalty may remain at 0 until time T10 when another message which has the particular subject matter may be presented to the user.

FIG. 6C is a graph 630 that illustrates changes to a score (e.g., a presentation score) of a message over time, in accordance with one or more embodiments. The x-axis of the graph 630 represents time, ranging from 0 to T_X. The y-axis of the graph 630 represents the value of the score, ranging from 0 to 1. As discussed above, the presentation score may be for a particular message for a user in a health/activity monitoring platform. As illustrated in graph 630, the score (e.g., presentation score) may start at the value 0.75 (e.g., a base score) until time T1. At time T1, the message may be presented to the user and the score for the message may decreased to 0 (e.g., a recency penalty may be applied to the base score). The score may remain at 0 between T1 and T2. For example, the time between T1 and T2 may be a blackout period where the message should not be presented again to the user (As discussed above). The score may remain at 0 (or may not increase) until the blackout period elapses.

At time T2, the score begins to increase. For example, a repetition penalty for the particular message and a subject matter penalty may begin to decrease due to a recency penalty decay rate and a subject matter penalty decay rate, respectively. At time T3, the rate at which the score increase may change. For example, the subject matter penalty for the topic/subject matter of the message may be decreased (e.g., decayed) to its lowest value (e.g., 0) but the recency penalty may still be greater than 0 so the recency penalty may continue to decrease. At time T4, the message may be presented to the user again and the score for the message may decreased to 0. The score may remain at 0 between T4 and T5 (due to a blackout period). At time T5, the score may increase due the recency penalty decay rate. At time T6, the rate of increase of the score may change due to the recency penalty decay rate and the subject matter penalty decay rate. At time T7, the message may be presented to the user again and the score for the message may decreased to 0.

FIG. 7A is a graph 710 that illustrates messages which may be identified for a user of the health/activity monitoring platform, in accordance with one or more embodiments. As discussed above, the health/activity monitoring platform (e.g., a message module, an identification module, etc.) may periodically identify a set of messages and/or may identify the set of messages based on events and/or triggers. Graph 710 may illustrate the messages that are identified for a user one day after a user begins using the health/activity monitoring platform. For example, the user may be new to the health/activity monitoring platform and the health/activity monitoring platform may not have collected much data (e.g., physiological data, behavioral data, environmental data, feedback data, etc.) on the user.

Each dot in the graph 710 may represent a message (that has been identified for the user). The lines (e.g., connections between the dots (e.g., messages) may indicate that the messages have the same topic/subject matter. As illustrated in FIG. 7A, three messages have been identified for the user and all of the messages (e.g., dots) are within the circle 751. This may indicate that all of the messages within the circle 751 have the same topic/subject matter (e.g., Sleep Debt, Circadian Rhythm, etc.).

FIG. 7B is a graph 720 that illustrates messages which may be identified for a user of the health/activity monitoring platform, in accordance with one or more embodiments. As discussed above, the health/activity monitoring platform (e.g., a message module, an identification module, etc.) may periodically identify a set of messages and/or may identify the set of messages based on events and/or triggers. Graph 720 may illustrate the messages that are identified for a user three days after a user begins using the health/activity monitoring platform. Each dot in the graph 720 may represent a message (that has been identified for the user). The size of the dots may represent the presentations scores for a respective message (e.g., the larger the dot, the higher the presentation score). The lines (e.g., connections between the dots (e.g., messages) may indicate that the messages have the same topic/subject matter.

As illustrated in FIG. 7B, seven messages have been identified for the user. Three of the messages are in the circle 751 (indicating that they are related to a first topic/subject matter), three of the messages are in the circle 752 (indicating that they are related to a second topic/subject matter) and one of the messages is in circle 752 (indicating that it is related to a third topic/subject matter).

FIG. 7C is a graph 730 that illustrates messages which may be identified for a user of the health/activity monitoring platform, in accordance with one or more embodiments. As discussed above, the health/activity monitoring platform (e.g., a message module, an identification module, etc.) may periodically identify a set of messages and/or may identify the set of messages based on events and/or triggers. Graph 730 may illustrate the messages that are identified for a user a week after a user begins using the health/activity monitoring platform. Each dot in the graph 730 may represent a message (that has been identified for the user). The size of the dots may represent the presentations scores for a respective message (e.g., the larger the dot, the higher the presentation score). The lines (e.g., connections between the dots (e.g., messages) may indicate that the messages have the same topic/subject matter.

As illustrated in FIG. 7C, sixteen messages have been identified for the user. Twelve of the messages are in the circle 751 (indicating that they are related to a first topic/subject matter), four of the messages are in the circle 752 (indicating that they are related to a second topic/subject matter) and one of the messages is in circle 752 (indicating that it is related to a third topic/subject matter). Also as illustrated in FIG. 7C, one message is related to both the first topic/subject matter and the second topic/subject matter (e.g., one dot is in both circle 751 and 752).

Figure 8A:
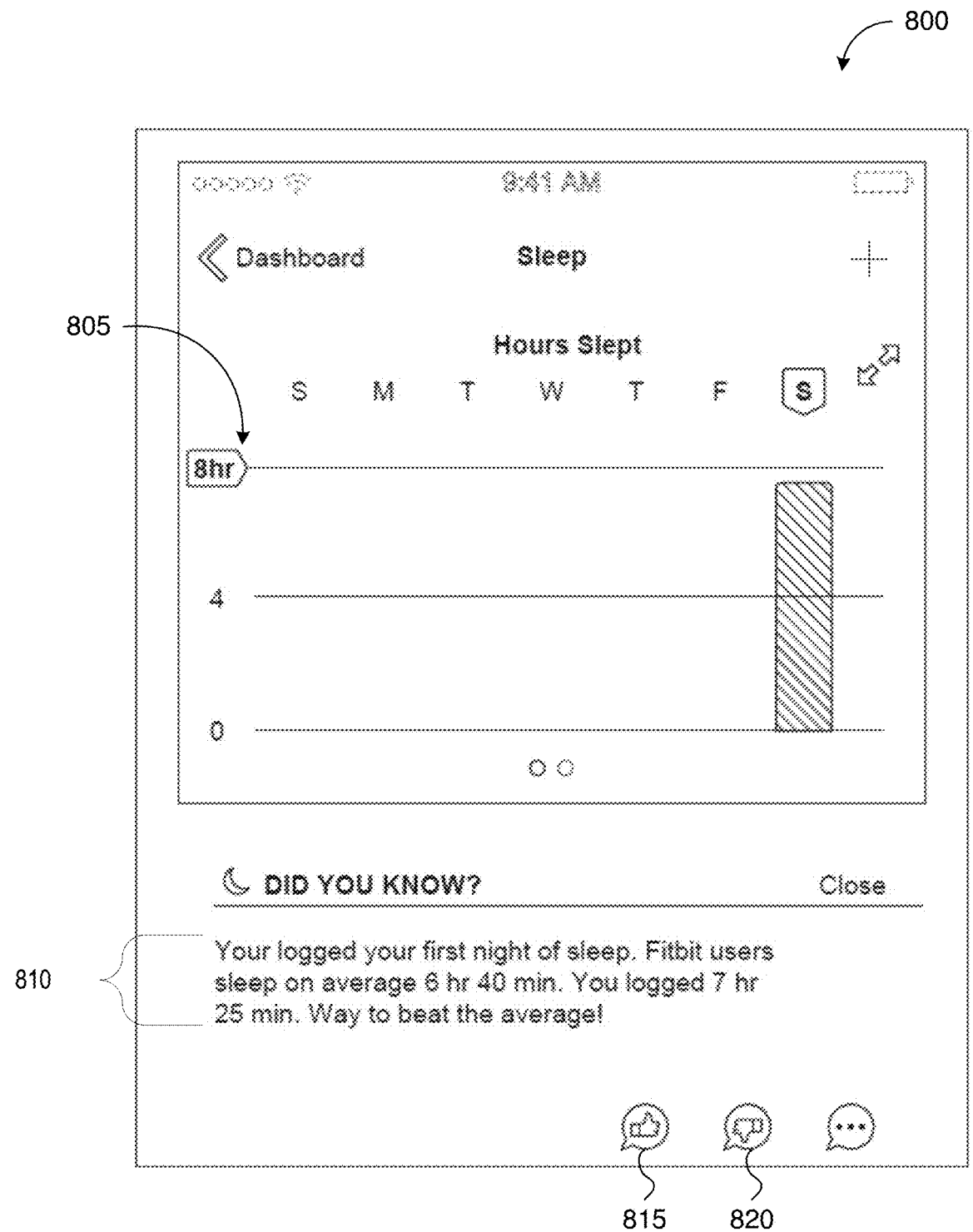
FIG. 8A illustrates an example graphical user interface (GUI), according to one or more embodiments.

FIG. 8A illustrates an example graphical user interface (GUI) 800, according to one or more embodiments. In one embodiment, the GUI 800 may be presented to a user by a health/fitness application on a computing device (e.g., an external computing device such as a laptop computer, a smartphone, a tablet computer, etc.). The GUI 800 may allow the health/activity monitoring platform to present messages, data, and/or other information, related to the health of the user, to the user. In some embodiments, the GUI 800 may be a webpage provided/presented by the health/activity monitoring platform. For example, the GUI 800 may be presented by and/or displayed within a web browser when the user accesses or logs into the health/activity monitoring platform via the web browser.

The GUI 800 includes a bar graph 805 which may indicate the numbers of hours a user slept for each day of a week. For example, as illustrated in FIG. 8A, the bar graph 805 may indicate that the user slept for 7 hours and 25 minutes on Saturday. The GUI 800 also includes message 810 (e.g., an insight, content, etc.) As discussed above, the message 810 may provide the user with health related information and/or content. For example, the message 810 may indicate the amount of time that the user has slept (e.g., 7 hours and 25 minutes) is more than the average amount of time that other users of the health/activity monitoring system sleep. The message 810 may be based on a template message and the actual amount of time that the user slept (e.g., 7 hours and 25 minutes) may be added to the template message to generate message 810, as discussed above.

The GUI 800 also includes button 815 and button 820. The buttons 815 and 820 may allow a user to provide feedback about the message 810. For example, the button 815 may allow the user to provide feedback indicating that the user liked the message 810 (e.g., approved of the message, found the message interesting or useful, etc.). In another example, button 820 may allow the user to provide feedback indicating that the user did not like the message 810 (e.g., did not approve of the messages, did not find the message interesting or useful, etc.).

Figure 8B:
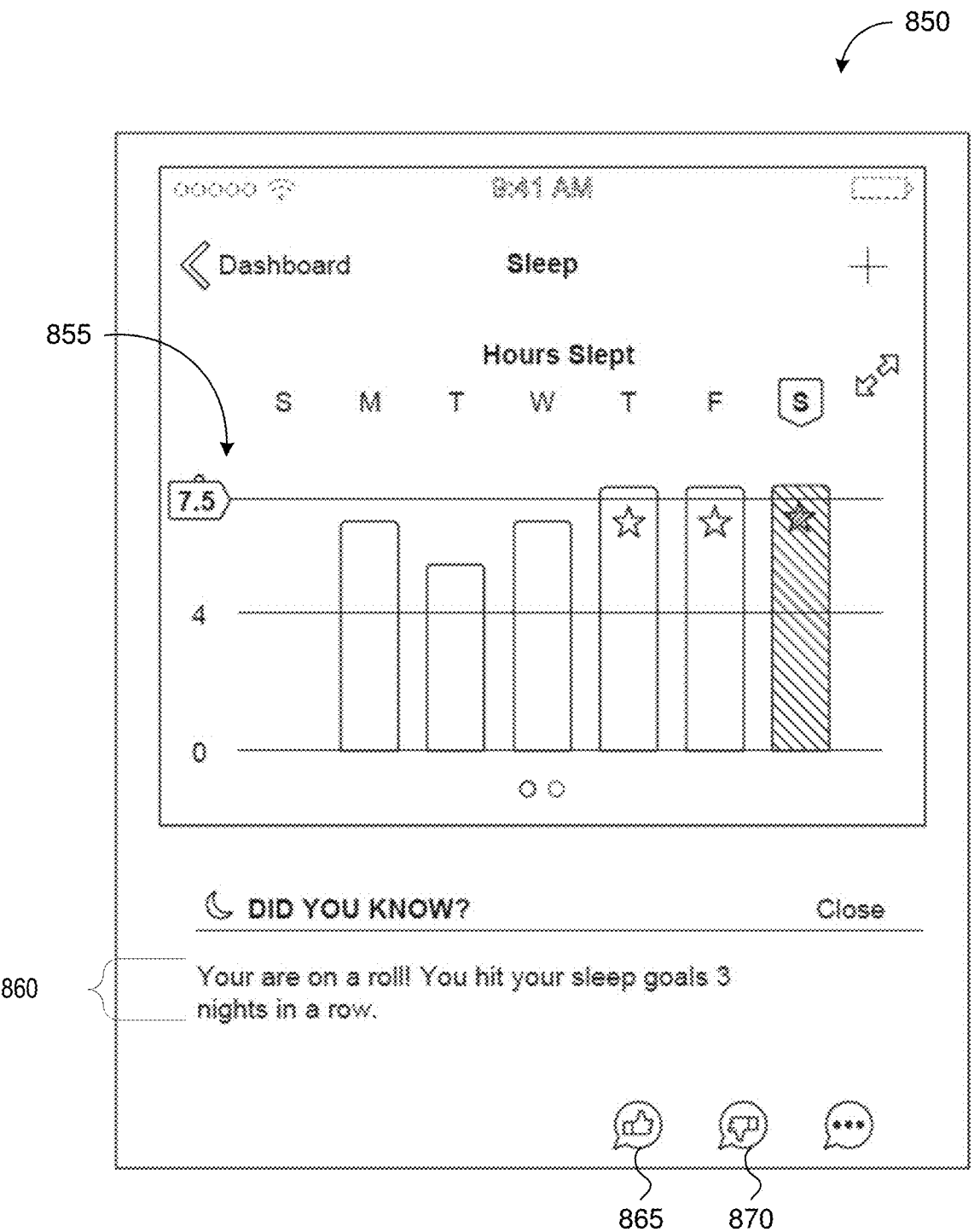
FIG. 8B illustrates an example GUI, in accordance with one or more embodiments.

FIG. 8B illustrates an example GUI 850, according to one or more embodiments. In one embodiment, the GUI 850 may be presented to a user by a health/fitness application on a computing device, as discussed above. The GUI 850 may allow the health/activity monitoring platform to present messages, data, and/or other information, related to the health of the user, to the user. In some embodiments, the GUI 850 may be a webpage provided/presented by the health/activity monitoring platform, as discussed above.

The GUI 850 includes a bar graph 855 which may indicate the numbers of hours a user slept for each day of a week. For example, as illustrated in FIG. 8B, the bar graph 855 may indicate that the user slept for approximately 7 hours on Monday, approximately 6.5 hours on Tuesday, etc. The GUI 850 also includes message 860 (e.g., an insight, content, etc.) As discussed above, the message 860 may provide the user with health related information and/or content. The message 860 may indicate that the user has met the user's sleep goal for the last three nights in a row (e.g., has been able to sleep a desired number of hours for the last three nights in a row). The message 860 may be based on a template message and the number of days that the user has met the user's sleep goal may be added to the template message to generate message 860, as discussed above. The GUI 850 also includes button 865 and button 870. The buttons 865 and 870 may allow a user to provide feedback about the message 860, as discussed above.

Figure 9A:
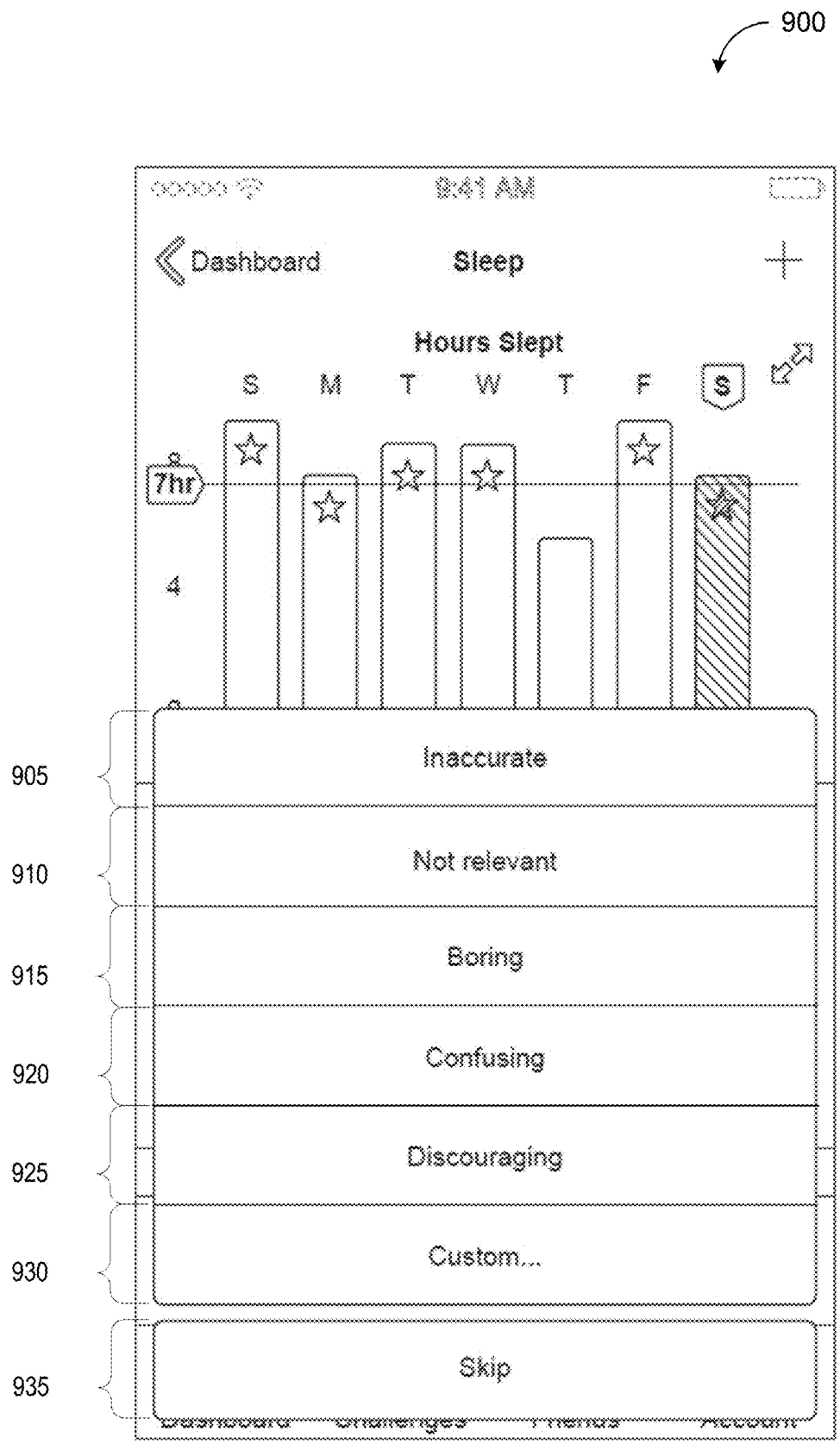
FIG. 9A illustrates an example GUI, in accordance with one or more embodiments.

FIG. 9A illustrates an example GUI 900, according to one or more embodiments. In one embodiment, the GUI 900 may be presented to a user by a health/fitness application on a computing device, as discussed above. The GUI 900 may allow the health/activity monitoring platform to present messages, data, and/or other information, related to the health of the user, to the user. In some embodiments, the GUI 900 may be a webpage provided/presented by the health/activity monitoring platform, as discussed above. Referring back to FIGS. 8A and 8B, the GUI 900 may be presented to the user when the button 820 and/or 870 is activated, clicked, pressed, selected, etc., by the user. The GUI 900 may allow the user to provide feedback indicating that the user did not like (e.g., did not approve of, did not find useful/interesting) a message that was presented to the user.

As illustrated in FIG. 9A, the GUI 900 includes button 905, button 910, button 915, button 920, button 925, button 930, and button 935. Button 905 may allow the user to indicate that the message was inaccurate. Button 910 may allow the user to indicate that the message was not relevant to the user. Button 915 may allow the user to indicate that the message was not interesting to the user. Button 920 may allow the user to indicate that the message was confusing to the user. Button 925 may allow the user to indicate that the message was discouraging to the user. Button 930 may allow the user to indicate a different reason why the user did not like the message. Button 935 may allow the user to skip providing a reason why the user did not like the message.

Figure 9B:
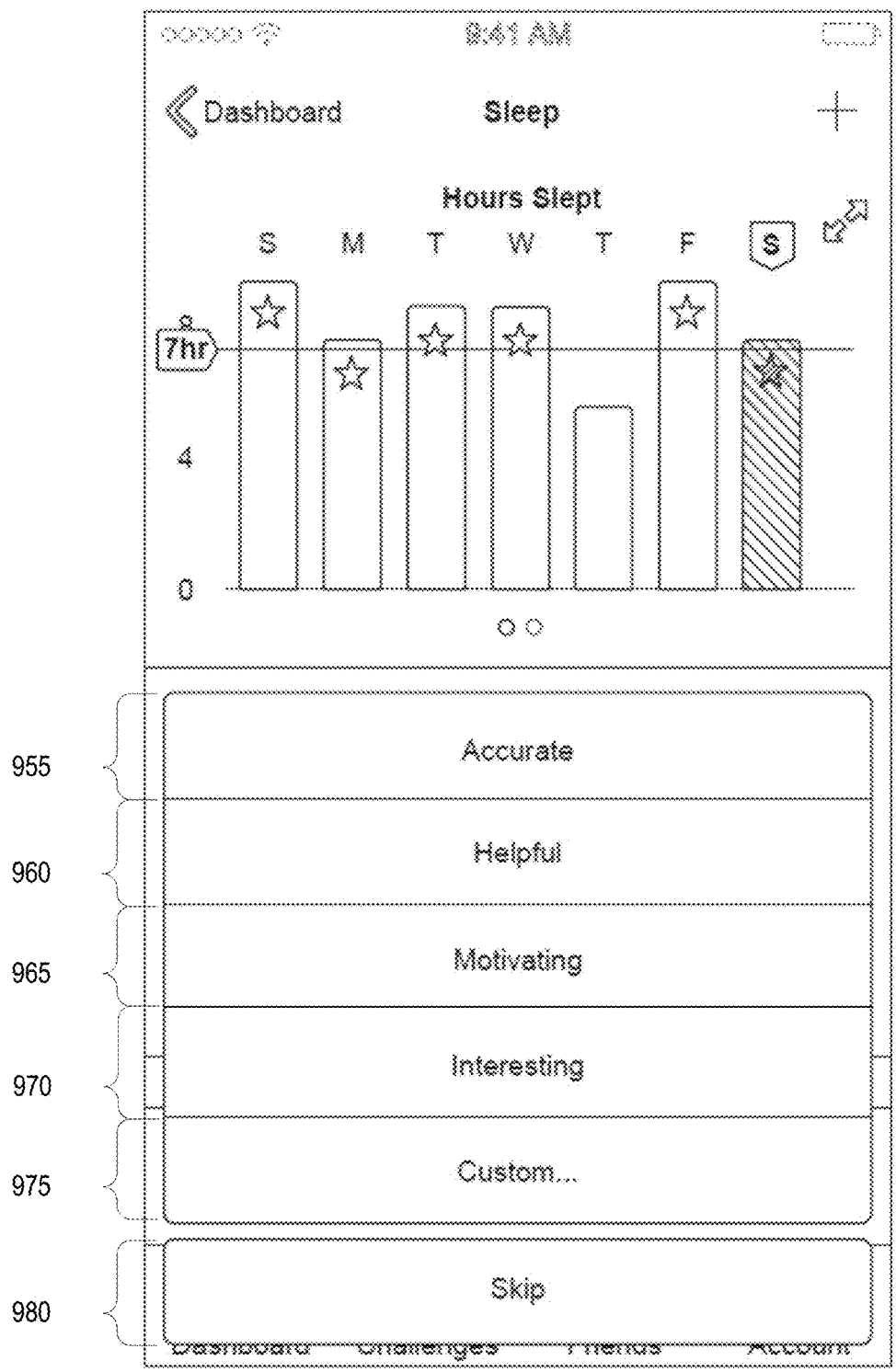
FIG. 9B illustrates an example GUI, in accordance with one or more embodiments.

FIG. 9B illustrates an example GUI 950, according to one or more embodiments. In one embodiment, the GUI 950 may be presented to a user by a health/fitness application on a computing device, as discussed above. The GUI 950 may allow the health/activity monitoring platform to present messages, data, and/or other information, related to the health of the user, to the user. In some embodiments, the GUI 950 may be a webpage provided/presented by the health/activity monitoring platform, as discussed above. Referring back to FIGS. 8A and 8B, the GUI 950 may be presented to the user when the button 815 and/or 865 is activated, clicked, pressed, selected, etc., by the user. The GUI 900 may allow the user to provide feedback indicating that the user liked (e.g., approved of, found useful/interesting) a message that was presented to the user.

As illustrated in FIG. 9B, the GUI 950 includes button 955, button 960, button 965, button 970, button 975, and button 980. Button 955 may allow the user to indicate that the message was accurate. Button 960 may allow the user to indicate that the message was helpful to the user. Button 965 may allow the user to indicate that the message was motivating to the user. Button 970 may allow the user to indicate that the message was interesting to the user. Button 975 may allow the user to indicate a different reason why the user like the message. Button 980 may allow the user to skip providing a reason why the user liked the message.

Figure 10:
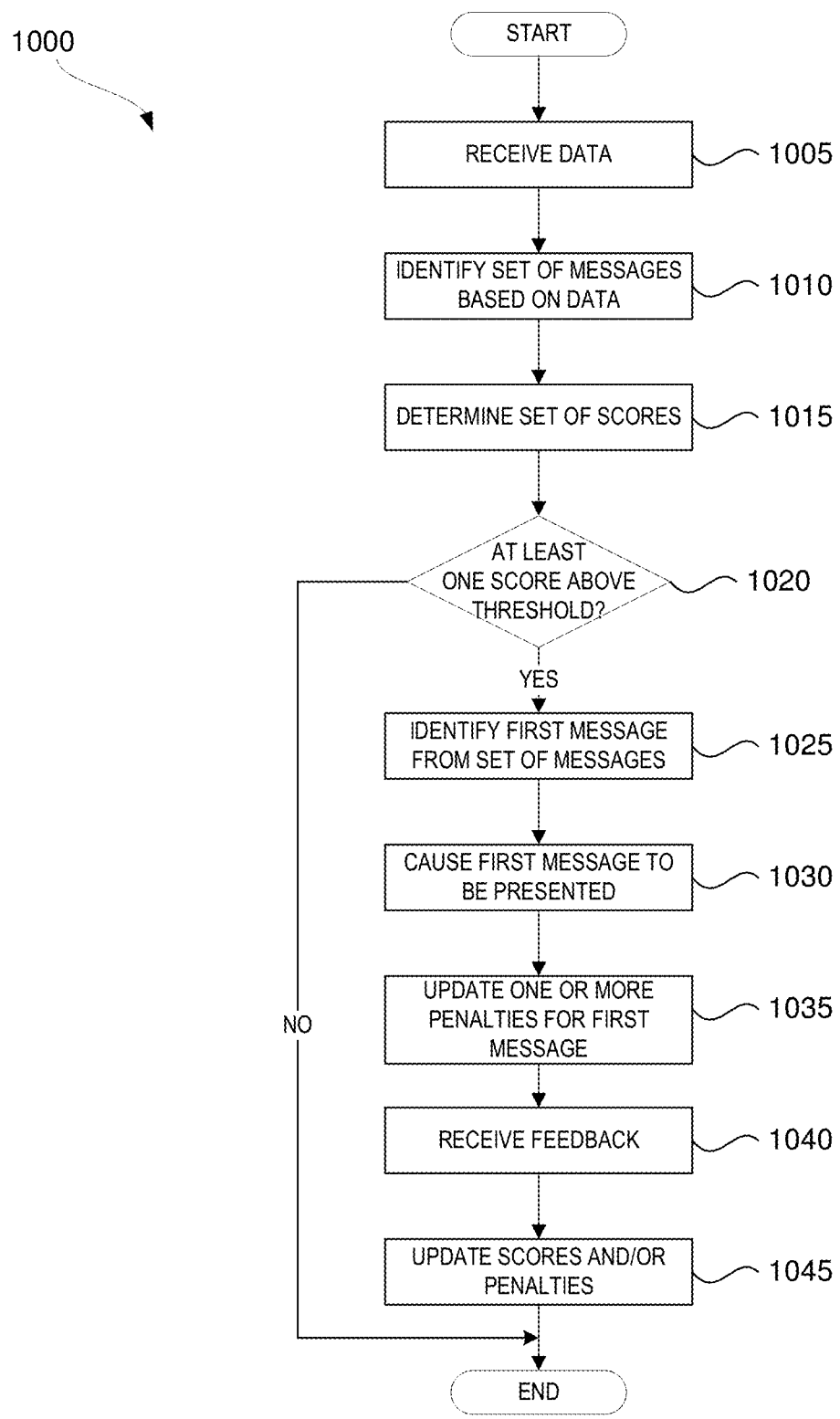
FIG. 10 is a flow diagram illustrating a process for presenting messages to a user, in accordance with one or more embodiments.

FIG. 10 is a flow diagram illustrating a process 1000 for presenting messages to a user of a health/activity monitoring platform, in accordance with one or more embodiments. The process 1000 may be performed by a message module, an identification module, a scoring module a deliver module, and a penalty module (e.g., the modules illustrated in FIGS. 4 and 5), a processing device (e.g., a processor, a central processing unit (CPU)), and/or a computing device (e.g., a server system/computer). The modules, processing device, and/or computing device may be processing logic that includes hardware (e.g., circuitry, dedicated logic, programmable logic, microcode, etc.), software (e.g., instructions run on a processor to perform hardware simulation), firmware, or a combination thereof.

1005 where the process 1005 receives data for a user. For example, the process 1005 may receive one or more of physiological data, environmental data, behavioral data, and feedback data, collected for a user (as discussed above. At block 1010, the process 1000 may identify a set of messages based on the received data. For example, the process 1000 may identify messages with topics/subject matters that may be of interest to a user based on one or more of the physiological data, environmental data, behavioral data, and feedback data, as discussed above. In another example, analyze the data (e.g., physiological data) to determine whether any events and/or triggers occurred. The process 1000 may identify a set of messages based on the events and/or triggers. As discussed above, the set of messages may be a subset of all of the messages that are available in the health/activity monitoring platform.

At block 1015, the process 1000 may determine a set of scores for set of messages that was identified. As discussed above, the process 1000 may determine one or more of a base score, a recency penalty, a repetition penalty, and subject matter penalties for each message in the set of messages. For example, the process 1000 may use the message data (e.g., message data 425 illustrated in FIGS. 4 and 5, Table 1 and Table 2 illustrated above, etc.) to determine one or more of a base score, a recency penalty, a repetition penalty, and subject matter penalties for a message. The process 1000 may use various equations and/or formulas (e.g., equations (1)-(7)) to determine (e.g., calculate) a score (e.g., a presentation score) for each message in the set of messages.

At block 1020, the process 1000 may determine whether at least one score in the set of scores is above a threshold score (e.g., whether at least one score in the set of scores meets a minimum score threshold). If there is no score in the set of scores that is above the threshold, the process 1000 may end. For example, the process 1000 may refrain from identifying a first message from the set of messages and causing the first message to be presented to a user. If there is at least one score in the set of scores that is above the threshold, the process 1000 may proceed to block 1025. In some embodiments, block 1020 may be optional. The process 1000 may identify a first message from the set of messages at block 1025. The first message may have the highest score in the set of scores, as discussed above. In one embodiment, the process 1000 may update the content of the first message to include information based on one or more of the physiological data, environmental data, behavioral data, and feedback data. For example, the process 1000 may update the content of the first message to include the actual number of hours a user slept last evening.

At block 1030, the process 1000 may cause the first message to be presented to a user. For example, the process 1000 may transmit the first message to an external computing device (e.g., a table computer, smartphone, etc.) of the user and/or to a wearable computing device of the user. The external computing device may present the message to the user via a GUI. For example, referring to FIGS. 8A and 8B, a GUI may be presented by a health/fitness application on the external computing device of the user and the GUI may present (e.g., display) the first message. The process 1000 may update the one or more penalties for the first message at block 1035. For example, the process 1000 may update one or more of a recency penalty, a repetition penalty, and subject matter penalties for the first message (as discussed above).

At block 1040, the process 1000 may receive feedback from the user. For example, the process 1000 may receive user feedback indicating whether the user liked/disliked the first message. As discussed above in conjunction with FIGS. 8A, 8B, 9A, and 9B, the user may use GUIs presented by the health/fitness application to provide the feedback. The process 1000 may update one or more scores and/or penalties for messages of the health/activity monitoring platform, based on the feedback. For example, the process 1000 may increase the base scores of messages with the same topic/subject matter as the first message based on user feedback indicating that the user liked the first message. After block 1045, the process 1000 ends.

Figure 11:
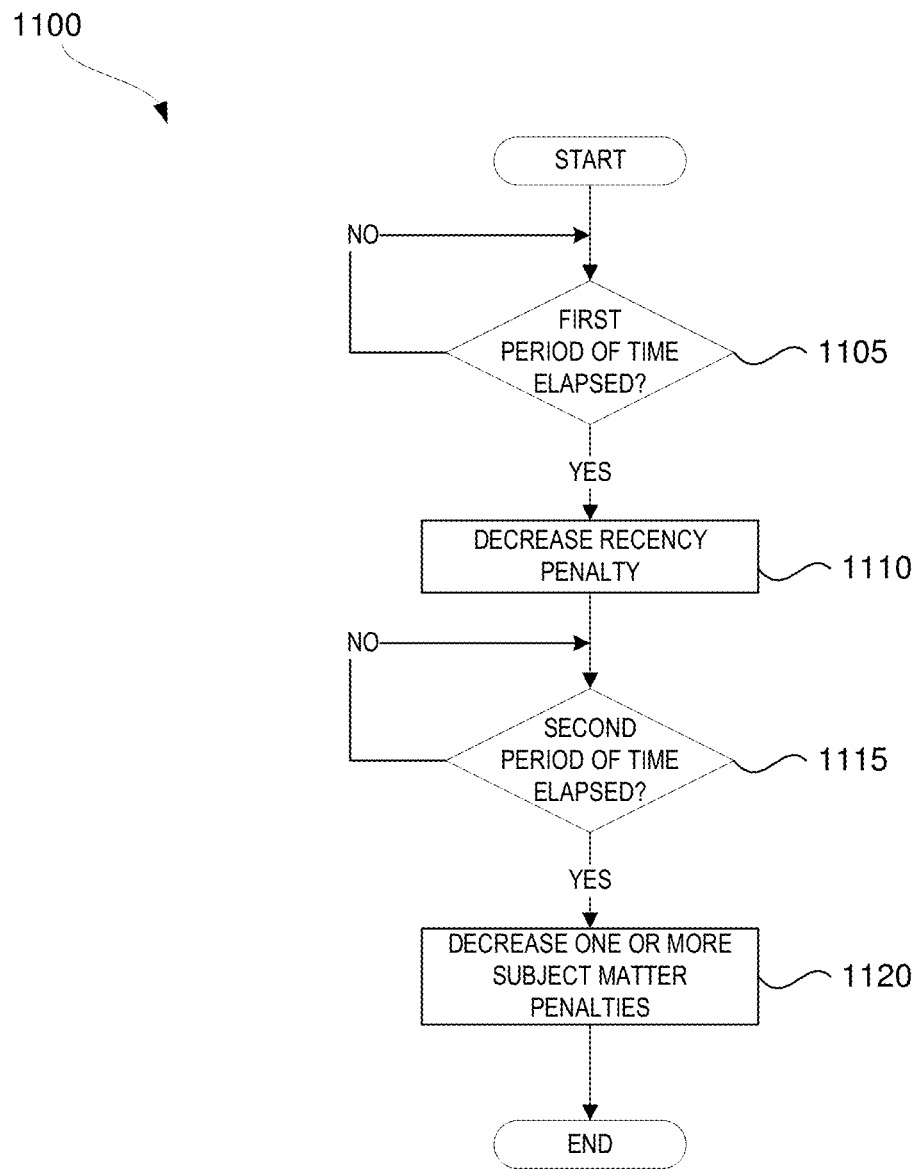
FIG. 11 is a flow diagram illustrating a process for updating one or more penalties, in accordance with one or more embodiments.

FIG. 11 is a flow diagram illustrating a process 1100 for updating one or more penalties, in accordance with one or more embodiments. The process 1000 may be performed by a message module, an identification module, a scoring module a deliver module, and a penalty module (e.g., the modules illustrated in FIGS. 4 and 5), a processing device (e.g., a processor, a central processing unit (CPU)), and/or a computing device (e.g., a server system/computer). The modules, processing device, and/or computing device may be processing logic that includes hardware (e.g., circuitry, dedicated logic, programmable logic, microcode, etc.), software (e.g., instructions run on a processor to perform hardware simulation), firmware, or a combination thereof.

The process 1100 begins at block 1105 where the process 1100 determines whether a first period of time has elapsed. For example, the process 1100 may determine whether an hour, a day, a week, two weeks, a month, etc., has elapsed. The duration of the first period of time (e.g., a day, a week, etc.) may be determined based on a recency penalty decay rate of a first message, as discussed above. For example, if the recency penalty decay rate indicates that the recency penalty should be decreased by 0.1 every 2 days, the process 1100 may determine whether 2 days has elapsed. If the first period of time has not elapsed, the process 1100 may proceed back to block 1105. If the first period of time has elapsed, the process 1100 may decrease a recency penalty for the first message based on the recency penalty decay rate at block 1110. For example, based on the recency penalty decay rate of 0.1 every 2 days, the process 1100 may decrease the recency penalty by 0.1.

At block 1115 where the process 1100 determines whether a second period of time has elapsed. For example, the process 1100 may determine whether an hour, a day, a week, two weeks, a month, etc., has elapsed. The duration of the second period of time (e.g., a day, a week, etc.) may be determined based on a subject matter penalty decay rate, as discussed above. For example, if the subject matter penalty decay rate indicates that a subject matter penalty should be decreased by 0.05 every week, the process 1100 may determine whether 1 week has elapsed. If the second period of time has not elapsed, the process 1100 may proceed back to block 1115. If the second period of time has elapsed, the process 1100 may decrease a subject matter penalty for the subject matter based on the subject matter penalty decay rate at block 1120. For example, based on the recency penalty decay rate of 0.05 every week, the process 1100 may decrease the subject matter penalty (for a topic/subject matter) by 0.05. After block 1120, the process 1100 ends.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Certain methods and/or processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

Reference throughout this specification to "certain embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the examples, embodiments, and/or implementations herein disclosed and claimed below should not be limited by the particular embodiments described above, but should be determined only by a fair reading of the claims that follow.

What is claimed is:

1. A method of presenting messages to a user, the method comprising:

receiving, by an external computing device over a network, physiological data comprising physiological characteristics relating to sleeping patterns of the user while the user sleeps, generated by one or more physiological sensors arranged on a protrusion of a backside of a biometric monitoring device worn by the user such that the one or more physiological sensors contact the user's skin with more force than remaining portions of the biometric monitoring device;

identifying, by the external computing device, a set of messages based on the physiological characteristics relating to sleeping patterns of the user, wherein each message in the set of messages comprises content associated with sleep of the user;

determining, by at least one software module of the external computing device and executed by a processor and applying at least one algorithm using a runtime multiplier, a set of scores for the set of messages, wherein each score from the set of scores is associated with a message from the set of messages and wherein each score from the set of scores is indicative of whether a respective message should be presented to the user;

identifying, by the external computing device, a first message from the set of messages based on the set of scores;

causing, by the external computing device communicating with the biometric monitoring device over the network, the first message to be presented via a graphical user interface (GUI) of a display of the biometric monitoring device of the user;

determining, by the external computing device, that an interaction of the user with the GUI is received, the interaction including feedback from the user in response to the first message; and automatically updating, by the least one software module of the external computing device, a first set of penalties associated with the first message in response to causing the first message to be presented, wherein at least one of the first set of penalties or the feedback for the first message decreases a first likelihood that the first message will be presented to the user again.

2. The method of claim 1, wherein each score from the set of scores is determined based on a respective base score and a respective set of penalties for each score.

3. The method of claim 2 wherein the first message is associated with a highest score from the set of scores.

4. The method of claim 1, wherein the first set of penalties comprises:
a recency penalty;
a repetition penalty; and
one or more subject matter penalties.

5. The method of claim 4, wherein updating the first set of penalties comprises:
identifying one or more subject matter identifiers for the first message; and
identifying the one or more subject matter penalties based on the one or more subject matter identifiers.

6. The method of claim 5, wherein updating the first set of penalties comprises:
increasing the recency penalty;
increasing the repetition penalty; and
increasing each of the one or more subject matter penalties.

7. The method of claim 6, further comprising:
determining whether a first period of time has elapsed; and
decreasing the recency penalty in response to a determination that the first period of time has elapsed.

8. The method of claim 7, further comprising:
determining whether a second period of time has elapsed; and
decreasing each of the one or more subject matter penalties in response to a determination that the second period of time has elapsed.

9. The method of claim 1, wherein the set of messages is identified further based on previous user feedback of one or more previous messages presented to the user.

10. The method of claim 1, wherein the set of messages is identified further based on user preferences of the user.

11. The method of claim 1, wherein the set of messages is identified further based on subject matter identifiers associated with the set of messages.

12. The method of claim 1, further comprising updating a first content of the first message to include personalized information associated with the sleep of the user based on the physiological data.

13. The method of claim 1, further comprising:
receiving user feedback for the first message; and
updating one or more of a set of base scores or a set of penalties for one or more messages based on the user feedback.

14. The method of claim 1, wherein the external computing device comprises one or more of a mobile device or a server system.

15. The method of claim 1, wherein the first message is identified further based on prerequisite messages associated with the first message.

16. The method of claim 1, wherein the first message was previously presented to the user and wherein a threshold number of messages have been presented to the user after the first message was previously presented to the user.

17. The method of claim 1, further comprising refraining from identifying the first message when each score from the set of scores is below a threshold score.

18. The method of claim 1, wherein the set of messages is identified further based on user feedback of one or more previous messages presented to other users.

19. The method of claim 1, wherein the set of messages is identified further based on estimated preferences of the user determined based on one or more of physiological data of the user or behavioral data of the user.

20. The method of claim 1, wherein the set of messages is identified further based on behavioral data of the user.

21. An external computing device, comprising:
a memory configured to store data; and
a processor coupled to the memory, the processor configured to:
receive, over a network, physiological data comprising physiological characteristics relating to sleeping patterns of the user while the user sleeps, generated by one or more physiological sensors arranged on a protrusion of a backside of a biometric monitoring device worn by the user such that the one or more physiological sensors contact the user's skin with more force than remaining portions of the biometric monitoring device;
identify a set of messages based on the physiological characteristics relating to sleeping patterns of the user, wherein each message in the set of messages comprises content associated with sleep of the user;
determine, by at least one software module executed by the processor and applying at least one algorithm using a runtime multiplier, a set of scores for the set of messages, wherein each score from the set of scores is associated with a message from the set of messages and wherein each score from the set of scores is indicative of whether a respective message should be presented to the user;
identify a first message from a set of messages based on the set of scores;
cause the first message to be presented via a graphical user interface (GUI) of a display of the biometric monitoring device of the user by communicating with the biometric monitoring device over the network;
determine that an interaction of the user with the GUI is received, the interaction including feedback from the user in response to the first message; and
automatically update, by the at least one software module, a first set of penalties associated with the first message in response to causing the first message to be presented, wherein at least one of the first set of penalties or the feedback decreases a first likelihood that the first message will be presented to the user again.

22. The apparatus of claim 21, wherein each score from the set of scores is determined based on a respective base score and a respective set of penalties for each score.

23. The apparatus of claim 21, wherein the first set of penalties comprises:
a recency penalty;
a repetition penalty; and
one or more subject matter penalties.

24. The apparatus of claim 23, wherein the processor is configured to update the first set of penalties by:

identifying one or more subject matter identifiers for the first message; and identifying the one or more subject matter penalties based on the one or more subject matter identifiers.

25. The apparatus of claim 24, wherein the processor is configured to update the first set of penalties by:

increasing the recency penalty;

increasing the repetition penalty; and increasing each of the one or more subject matter penalties.

26. The apparatus of claim 25, wherein the processor is further configured to:

determine whether a first period of time has elapsed; and decrease the recency penalty in response to a determination that the first period of time has elapsed.

27. A non-transitory computer readable storage medium comprising instructions that, when executed by a processor, cause the processor to perform operations comprising:

receiving, over a network, physiological data comprising physiological characteristics relating to sleeping patterns of the user while the user sleeps, generated by one or more physiological sensors arranged on a protrusion of a backside of a biometric monitoring device worn by the user such that the one or more physiological sensors contact the user's skin with more force than remaining portions of the biometric monitoring device;

identifying a set of messages based on the physiological characteristics relating to sleeping patterns of the user, wherein each message in the set of messages comprises content associated with sleep of the user;

determining, by at least one software module executed by the processor and applying at least one algorithm using a runtime multiplier, a set of scores for the set of messages, wherein each score from the set of scores is associated with a message from the set of messages and wherein each score from the set of scores is indicative of whether a respective message should be presented to the user;

identifying a first message from a set of messages based on the set of scores;

causing the first message to be presented via a graphical user interface (GUI) of a display of the biometric monitoring device of the user by communicating with the biometric monitoring device over the network;

determining that an interaction of the user with the GUI is received, the interaction including feedback from the user in response to the first message; and automatically updating, by the at least one software module, a first set of penalties associated with the first message in response to causing the first message to be presented, wherein at least one of the first set of penalties or the feedback decreases a first likelihood that the first message will be presented to the user again.

* * * * *